(12) United States Patent
Leffak et al.

(10) Patent No.: US 7,851,153 B2
(45) Date of Patent: Dec. 14, 2010

(54) DNA BINDING PROTEIN

(75) Inventors: Michael Leffak, Dayton, OH (US); John Casper, Dayton, OH (US)

(73) Assignee: Wright State University, Dayton, OH (US)

( * ) Notice: Subject to any disclaimer, the term of this patent is extended or adjusted under 35 U.S.C. 154(b) by 451 days.

(21) Appl. No.: 11/291,360

(22) Filed: Dec. 1, 2005

(65) Prior Publication Data

US 2006/0084108 A1 Apr. 20, 2006

Related U.S. Application Data

(62) Division of application No. 10/487,964, filed as application No. PCT/US02/27809 on Aug. 30, 2002, now abandoned.

(60) Provisional application No. 60/316,496, filed on Aug. 31, 2001.

(51) Int. Cl.
*C12Q 1/68* (2006.01)
(52) U.S. Cl. .......................................... 435/6; 536/23.5
(58) Field of Classification Search ....................... None
See application file for complete search history.

(56) References Cited

U.S. PATENT DOCUMENTS

| | | | |
|---|---|---|---|
| 5,217,864 A | 6/1993 | Heintz et al. | |
| 5,958,671 A * | 9/1999 | Glimcher et al. | ............... 435/4 |
| 2004/0203109 A1 | 10/2004 | Lal et al. | |

OTHER PUBLICATIONS

Duncan et al., "A sequence-specific, single -strand binding protein activates the far upstream element of c-myc and defines a new DNA-binding motif", Genes & Development 8, 1994, pp. 465-480.
Whinney et al., "Cis-Acting Effects of Sequences Within 2.4kb Upstream of the Human c-myc Gene on Autonomous Plasmid Replication in HeLa Cells", DNA and Cell Biology, vol. 14, No. 7, 1995, pp. 565-579.
Trivedi et al., "Multiple Initiations in the c-myc Replication Origin Independent of Chromosomal Location", DNA and Cell Biology, vol. 17, No. 10, 1998, pp. 885-896.
Newlon et al., "The structure and function of yeast ARS elements", Current Opinion in Genetics and Development, 1993, 3, pp. 752-758.
Hartwell et al., "Cell Cycle Control and Cancer", Science, vol. 266, Dec. 16, 1994, pp. 1821-1828.
Kumar et al., "Conserved Chromatin Structure in c-myc 5-Flanking DNA after Viral Transduction", J. Mol. Biol. (1991), 222, pp. 45-57.
Tao et al., "Major DNA Replication Initiation Sites in the c-myc Locus in Human Cells", Journal of Cellular Biochemistry, 2000, 78, pp. 442-457.
Walter et al., "Regulated Chromosomal DNA Replication in the Absence of a Nucleus", Molecular Cell, vol. 1, Mar. 1998, pp. 519-529.
Walter et al., Initiation of Eukaryotic DNA Replication: Origin Unwinding and Sequential Chromatin Association of Cdc45, RPA, and DNA Polymerase α, Molecular Cell, vol. 5, Apr. 2000, pp. 617-627.
Tao et al., "Differential DNA Replication Origin Activities in Human Normal Skin Fibroblast and HeLa Cell Lines", J. Mol. Biol. (1997), 273, pp. 509-519.
Rein et al., "DNA Methylation at Mammalian Replication Origins", The Journal of Biological Chemistry, vol. 274, No. 36, Sep. 3, 1999, pp. 25792-25800.
Phi-Van et al., "An Initiation Zone of Chromosomal DNA Replication at the Chicken Lysozyme Gene Locus", The Journal of Biological Chemistry, vol. 273, No. 29, Jul. 17, 1998, pp. 18300-18307.
Michelotti et al., "Multiple Single-Stranded cis Elements Are Associated with Activated Chromatin of the Human c-myc Gene In Vivo", Molecular and Cellular Biology, vol. 16, No. 6, Jun. 1996, pp. 2656-2669.
McWhinney et al., "Autonomous replication of a DNA fragment containing the chromosomal replication origin of the human c-myc gene", Nucleic Acids Research, vol. 18, No. 5, 1990, pp. 1233-1242.
Malott et al., "Activity of the c-myc Replicator at an Ectopic Chromosomal Location", Molecular and Cellular Biology, vol. 19, No. 8, Aug. 1999, pp. 5685-5695.
Kumar et al., "DNA topology of the ordered chromatin domain 5' to the human c-myc gene", Nucleic Acids Research, vol. 17, No. 7, 1989, pp. 2819-2833.
Leffak et al., "Opposite Replication Polarity of the Germ Line c-myc Gene in HeLa Cells Compared with that of Two Burkitt Lymphoma Cell Lines", Molecular and Cellular Biology, vol. 9, No. 2, Feb. 1989, pp. 586-593.
Ishimi et al., "DNA Replication from Initiation Zones of Mammalian Cells in a Model System", Molecular and Cellular Biology, Oct. 1994, pp. 6489-6496.
Dobbs et al., "Modular sequence elements associated with origin regions in eukaryotic chromosomal DNA", Nucleic Acids Research, 1994, vol. 22, No. 13, pp. 2479-2489.
Cimbora et al., "The Control of Mammalian DNA Replication: A Brief History of Space and Timing", Cell, vol. 104, Mar. 9, 2001, pp. 643-646.
Berberich et al., "In Vitro Replication of Plasmids Containing Human c-myc DNA", J. Mol. Biol., 245, 1995, pp. 92-109.
Bazar et al., "Targeted Melting and Binding of a DNA Regulatory Element by a Transactivator of c-myc", The Journal of Biological Chemistry, vol. 270, No. 14, Apr. 7, 1995, pp. 8241-8248.
Vassilev et al., "An Initiation Zone of Chromosomal DNA Replication Located Upstream of the c-myc Gene in Proliferating HeLa Cells", Molecular and Cellular Biology, vol. 10, No. 9, Sep. 1990, pp. 4899-4904.
Munder et al., "Yeast cells as tools for target-oriented screening" Appl Microbiol Biotechnol (1999) vol. 52, pp. 311-320.

* cited by examiner

*Primary Examiner*—James S Ketter
(74) *Attorney, Agent, or Firm*—Dinsmore & Shohl LLP

(57) ABSTRACT

Methods of screening for compounds which are, for example, capable of modulating amino acid-DNA interaction, modulating DNA replication, modulating cell proliferation, and for identifying compounds which inhibit cellular proliferation caused by cancer, are provided.

12 Claims, 24 Drawing Sheets

```
1     ATCCTTAATTAAATTAATCTTCCCCCCCCGGACCGAGTCGGACCGGCCAGTTGGGCGCGC
      TTCCGGGTGTCACCTCCAGAGGGCGCCGGCTGCGGAGCCGCCCTCAGAGTCGCGAGGCCG
121   GACGCAGCGCGGCGCCGCCCCACTCGCCCCAGCCGCCGCCATGAAGGCCGTGGTGCAGCG
                                          M  K  A  V  V  Q  R

181   CGTCACCCGGGCCAGCGTCACAGTTGGAGGAGAGCAGATTAGTGCCATTGGAAGGGCAT
  8    V  T  R  A  S  V  T  V  G  G  E  Q  I  S  A  I  G  R  G  I

241   ATGTGTGTTGCTGGGTATTTCCCTGGAGGATACGCAGAAGGAACTGGAACACATGGTCCG
 28    C  V  L  L  G  I  S  L  E  D  T  Q  K  E  L  E  H  M  V  R

301   AAAGATTCTAAACCTGCGTGTATTTGAGGATGAGAGTGGGAAGCACTGGTCGAAGAGTGT
 48    K  I  L  N  L  R  V  F  E  D  E  S  G  K  H  W  S  K  S  V

361   GATGGACAAACAGTACGAGATTCTGTGTGTCAGCCAGTTTACCCTCCAGTGTGTCCTGAA
 68    M  D  K  Q  Y  E  I  L  C  V  S  Q  F  T  L  Q  C  V  L  K

421   GGGAAACAAGCCTGATTTCCACCTAGCAATGCCCACGGAGCAGGCAGAGGGCTTCTACAA
 88    G  N  K  P  D  F  H  L  A  M  P  T  E  Q  A  E  G  F  Y  N

481   CAGCTTCCTGGAGCAGCTGCGTAAAACATACAGGCCGGAGCTTATCAAAGATGGCAAGTT
108    S  F  L  E  Q  L  R  K  T  Y  R  P  E  L  I  K  D  G  K  F

541   TGGGGCCTACATGCAGGTGCACATTCAGAATGATGGGCCTGTGACCATAGAGCTGGAATC
128    G  A  Y  M  Q  V  H  I  Q  N  D  G  P  V  T  I  E  L  E  S

601   GCCAGCTCCCGGCACTGCTACCTCTGACCCAAAGCAGCTGTCAAAGCTCGAAAAACAGCA
148    P  A  P  G  T  A  T  S  D  P  K  Q  L  S  K  L  E  K  Q  Q

661   GCAGAGGAAAGAAAAGACCAGAGCTAAGGGACCTTCTGAATCAAGCAAGGAAAGAAACAC
168    Q  R  K  E  K  T  R  A  K  G  P  S  E  S  S  K  E  R  N  T

721   TCCCCGAAAAGAAGACCGCAGTGCCAGCAGCGGGGCTGAGGGCGACGTGTCCTCTGAACG
188    P  R  K  E  D  R  S  A  S  S  G  A  E  G  D  V  S  S  E  R

781   GGAGCCGTAGCTCAGGAGGCAGAATTCAGTGTGTTATCATTGGGCAGAACTGGATCCTGA
208    E  P  *

841   AAAATTCAAGATGCTAAGCACCTACACTACTTTAAGAATTTGGAACTGAAACATGAAGAG
901   GAAGACAGAAATAAGAATTTGGAACCTGAATAGCTCTGCAAAAAACACCAAAGGACCGT
961   TTTATCGTTTTCTGTTGTTGCTGTGGTGGAGTGATGCAGTGGGCACTGCCAGTGGGCCAG
1021  GGGGCGGGTGCGCATGTGGTAGAAGGTGTGCGCTCGTGCCTCCCCCACAGAAAGGCTTTG
1081  TTGGTTTCTACCACÁTCTTGGCTTGCTTTTGGAACAGGCTGGCCCAGCATCATTTGTCAT
1141  CAAGTCCACTGTGGTGTATTCTGCGTGTCCATGGCGGGGGTTCTCCAACACACTCACACT
1201  GTCCATGTTCTTTTTATTGCCAGGGCCCGTGTTGAAGTGTCAAGAGAGCAATCATCAATG
1261  ATAATGTATTGTGTGAGACCTTTGCATCTTGTAAATTTTCTCTTTTTTCTAAAAATAAAT
1321  AATAATAAAATCCTAAAAAAAAAAAAA
```

Fig. 3

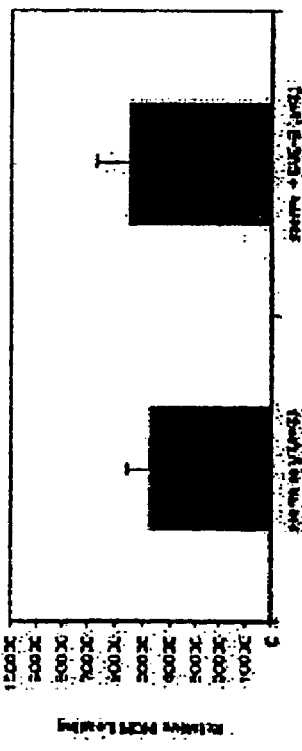
Fig. 20D
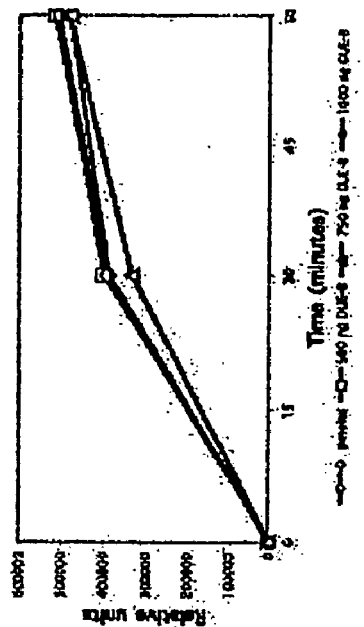
Fig. 20A
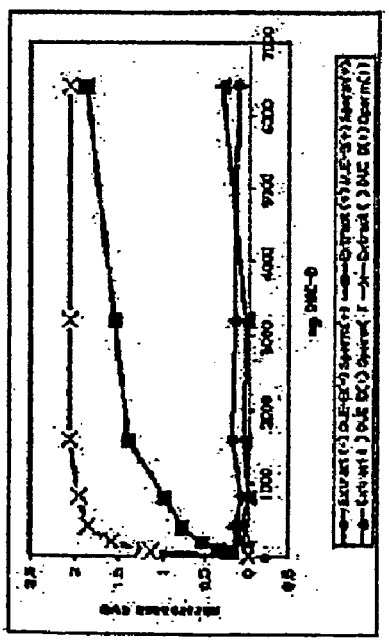
Fig. 20B
Fig. 20C

SEQUENCE LISTING

<160> NUMBER OF SEQ ID NOS: 7

<210> SEQ ID NO 1
<211> LENGTH: 1347
<212> TYPE: DNA
<213> ORGANISM: Homo sapiens

<400> SEQUENCE: 1

```
atccttaatt aaattaatct tcccccccg gaccgagtcg gaccggccag ttgggcgcgc      60
ttccgggtgt cacctccaga gggcgccggc tgcggagccg ccctcagaga cgcgaggccg     120
gacgcagcgc ggcgccgccc cactcgcccc agccgccgcc atgaaggccg tggtgcagcg     180
cgtcacccgg gccagcgtca cagttggagg agagcagatt agtgccattg aagggggcat     240
atgtgtgttg ctgggtattt ccctggagga tacgcagaag gaactggaac acatggtccg     300
aaagattcta aacctgcgag tatttgagga tgagagtggg aagcactggt cgaagagtgt     360
gatggacaaa cagtacgaga ttctgtgtgt cagccagttt accctccagt gtgtcctgaa     420
gggaaacaag cctgatttcc acctagcaat gcccacggag caggcagagg gcttctacaa     480
cagcttcttg gagcagctgc gtaaaacata caggccggag cttatcaaag atggcaagtt     540
tggggcctac atgcaggtgc acattcagaa tgatgggcct gtgaccatag agctggaatc     600
gccagctccc ggcactgcta cctctgaccc aaagcagctg tcaaagctcg aaaaacagca     660
gcagaggaaa gaaaagacca gagctaaggg accttctgaa tcaagcaagg aaagaaacac     720
tccccgaaaa gaagaccgca gtgccagcag cggggctgag ggcgacgtgt cctctgaacg     780
ggagccgtag ctcaggaggc agaattcagt gtgttatcat tgggcagaac tggatcctga     840
aaaattcaag atgctttgca cctacactac tttaagaatt tggaactgaa acatgaagag     900
gaagacagaa ataagaattt gggaacctga atagctctgc aaaaaacacc aaaggaccgt     960
tttatcgttt tctgttgttg ctgtggtgga gtgatgcagt gggcactgcc agtgggccag    1020
ggggcgggtg cgcatgtggt agaaggtgtg cgctcgtgcc tccccacag aaaggctttg    1080 ttggtttcta ccacatcttg gcttgctttt ggaacaggct ggcccagcat catttgtcat    1140
caagtccact gtggtgtatt ctgcgtgtcc atggcggggg ttctccaaca cactcacact    1200
gtccatgttc tttttattgc cagggccgt gttgaagtgt caagagagca atcaacaatg    1260
```

```
ataatgtatt gtgtgagacc tttgcatctt gtaaatttc tcttttttct aaaaataaat    1320
aataataaaa tcctaaaaaa aaaaaaa                                        1347
```

<210> SEQ ID NO 2
<211> LENGTH: 209
<212> TYPE: PRT
<213> ORGANISM: Homo sapiens

<400> SEQUENCE: 2

```
Met Lys Ala Val Val Gln Arg Val Thr Arg Ala Ser Val Thr Val Gly
1               5                   10                  15
Gly Glu Gln Ile Ser Ala Ile Gly Arg Gly Ile Cys Val Leu Leu Gly
            20                  25                  30
Ile Ser Leu Glu Asp Thr Gln Lys Glu Leu Glu His Met Val Arg Lys
        35                  40                  45
Ile Leu Asn Leu Arg Val Phe Glu Asp Glu Ser Gly Lys His Trp Ser
    50                  55                  60
Lys Ser Val Met Asp Lys Gln Tyr Glu Ile Leu Cys Val Ser Gln Phe
65                  70                  75                  80
Thr Leu Gln Cys Val Leu Lys Gly Asn Lys Pro Asp Phe His Leu Ala
                85                  90                  95
Met Pro Thr Glu Gln Ala Glu Gly Phe Tyr Asn Ser Phe Leu Glu Gln
            100                 105                 110
Leu Arg Lys Thr Tyr Arg Pro Glu Leu Ile Lys Asp Gly Lys Phe Gly
        115                 120                 125
Ala Tyr Met Gln Val His Ile Gln Asn Asp Gly Pro Val Thr Ile Glu
    130                 135                 140
Leu Glu Ser Pro Ala Pro Gly Thr Ala Thr Ser Asp Pro Lys Gln Leu
145                 150                 155                 160
Ser Lys Leu Glu Lys Gln Gln Arg Lys Glu Lys Thr Arg Ala Lys
                165                 170                 175
Gly Pro Ser Glu Ser Ser Lys Glu Arg Asn Thr Pro Arg Lys Glu Asp
            180                 185                 190
Arg Ser Ala Ser Ser Gly Ala Glu Gly Asp Val Ser Ser Glu Arg Glu
        195                 200                 205
Pro
```

<210> SEQ ID NO 3
<211> LENGTH: 30
<212> TYPE: DNA
<213> ORGANISM: Artificial Sequence
<220> FEATURE:
<223> OTHER INFORMATION: Probe for DUE-B

<400> SEQUENCE: 3

```
ggaatataca ttatatatta aatatagatc                                     30
```

<210> SEQ ID NO 4
<211> LENGTH: 98
<212> TYPE: DNA
<213> ORGANISM: Artificial Sequence
<220> FEATURE:
<223> OTHER INFORMATION: Wild type bait sequence

<400> SEQUENCE: 4

```
atgagaagaa tgttttttgt ttttcatgcc gtggaataac acaaaataaa aaatcccgag    60
ggaatataca ttatatatta aatatagatc atttcagg                             98
```

```
<210> SEQ ID NO 5
<211> LENGTH: 98
<212> TYPE: DNA
<213> ORGANISM: Artificial Sequence
<220> FEATURE:
<223> OTHER INFORMATION: ARS mutant bait sequence

<400> SEQUENCE: 5
atgagaagaa tgtttttgc gcttcatgcc gtggaataac acagcgtaaa aaatcccgag        60
ggaatataca ttatatattt gttatagatc atttcagg                              98

<210> SEQ ID NO 6
<211> LENGTH: 99
<212> TYPE: DNA
<213> ORGANISM: Artificial Sequence
<220> FEATURE:
<223> OTHER INFORMATION: DUE mutant / ARS mutant bait sequence

<400> SEQUENCE: 6
atgagaagaa tgtttttgc gcttcatgcc gtggaataac acagcgtaaa aaatcccgag        60
ggaatgcaca ttgcatattg cgcgtacgat catttcagg                             99

<210> SEQ ID NO 7
<211> LENGTH: 123
<212> TYPE: DNA
<213> ORGANISM: Artificial Sequence
<220> FEATURE:
<223> OTHER INFORMATION: c-myc DUE/ARS probe

<400> SEQUENCE: 7
gaaggaattc atgagaagaa tgtttttgt ttttcatgcc gtggaataac acaaaataaa        60
aaatcccgag ggaatataca ttatatatta aatatagatc atttcaggga gctcgagaaa     120
caa                                                                    123
```

DNA BINDING PROTEIN

CROSS-REFERENCES TO RELATED APPLICATIONS

This application is a divisional application of U.S. patent application Ser. No. 10/487,964 filed Feb. 26, 2004 which was a 35 U.S.C. § 371 of PCT Application No. PCT/US02/027809 which was filed on Aug. 30, 2002 and claimed priority to U.S. Patent Application No. 60/316,496 which was filed on Aug. 31, 2001.

FIELD OF THE INVENTION

This invention relates to methods of screening for compounds which are, for example, capable of modulating amino acid-DNA interaction, modulating DNA replication, modulating cell proliferation, and for identifying compounds which inhibit cellular proliferation caused by cancer.

BACKGROUND OF THE INVENTION

The process of DNA replication is the primary target of anticancer chemotherapy, since cancer cells, like normal cells, have to replicate their DNA in order to divide. Identification of the proteins that are needed for DNA replication can provide new candidates against which to design novel antitumor drugs. To date, most anticancer drugs have been directed against the enzymatic machinery of DNA systhesis. However, the genetic mutations that lead to cancer are rarely found in these enzymes. Instead, it is the genes involved in signaling pathways controlling the initiation of DNA synthesis during the cell cycle origin responding to errors of replication that are most often mutated in cancer cells.

Chromosomal replication origins are molecular switches, where the major regulated step of DNA synthesis, the initiation of replication, occurs. The applicants previously identified the origin of replication of the human c-myc gene. Characterization of the c-myc origin has led to the discovery of a new protein, called DNA Unwinding Element binding protein (DUE-B) that binds in vivo in a yeast one-hybrid assay to an important control site in the c-myc origin, the DNA unwinding element (DUE).

Other relevant protein complexes are known in the art. For instance, U.S. Pat. No. 5,217,864 describes a replication initiator protein complex for eukaryotic cells that comprises a purified protein complex capable of origin-specific DNA binding in vitro. While this protein has not been shown to function as such in vivo, it may be useful in the development of specific diagnostic and therapeutic applications, such as drug assays to identify inhibitors of S phase initiation.

However, no protein has been identified to date with the property of binding in vivo to a region of DNA that controls DNA replication. Accordingly, the need remains in the art for new ways to interfere with the cell division cycle.

It would therefore be desirable to identify a novel DNA binding protein for use as a target in pharmaceutical assays for chemotherapeutic drugs designed to inhibit tumor cell division, as well as to identify other compounds effective in enhancing or retarding cell division.

It would also be desirable to prepare antibodies or antibody derivatives that react with the DNA binding protein.

It would further be desirable to prepare cloned and purified forms of the DNA binding protein from bacterial and eukaryotic cells, as well as modified forms of such a protein fused or not to other polypeptides.

SUMMARY OF THE INVENTION

The present invention meets these needs by providing a novel, purified human protein that binds in vivo to the c-myc replication origin DNA unwinding element.

In accordance with one aspect of the present invention, an isolated nucleic acid molecule is provided comprising a nucleotide sequence encoding a human DNA binding protein, wherein the binding protein is DUE-B protein. The applicants have determined through other experiments that a certain region of DNA, the human chromosomal c-myc replication origin, regulates the initiation of DNA synthesis. The DUE-B protein has been shown to bind in vivo to this region.

Additional features of the present invention include the preparation of antibodies or antibody derivatives that react with the DUE-B protein, the preparation of cloned and purified DUE-B from bacterial and eukaryotic cells, and the identification of a frog (*Xenopus laevis*) protein related to human DUE-B. Still an additional feature of the present invention includes the preparation of modified forms of DUE-B fused to other polypeptides.

DUE-B mRNA and protein are present constitutively through the cell cycle. DUE-B expressed in HeLa cells is localized in the nucleus, and cell fractionation experiments indicate that a portion (~30-40%) of intracellular DUE-B is bound to chromatin. Roughly 90-95% of the endogenous DUE-B protein extractable from chromatin in HeLa cells associates to form dimers that comigrate on gel filtration with DUE-B expressed from a baculovirus vector. The remaining 5-10% of DUE-B extracted from HeLa cells migrates in a high molecular weight (>250 kDa) form. In contrast, human DUE-B expressed in bacteria chromatographs as 26 kDa monomers. In vitro, human baculovirus expressed DUE-B binds DNA and interacts with the c-myc DUE in conjunction with other, as yet unidentified, proteins. The human DUE-B gene comprises seven exons on chromosome 20. Sequencing of the DUE-B cDNA suggested the presence of an ATPase motif in the protein, and the ATPase activity has been confirmed. DUE-B is also a kinase substrate, consistent with the presence of seven casein kinase consensus target sites in the protein. The DUE-B gene shows strong homology across evolutionary boundaries, from bacteria to yeast, mice, and humans. The carboxyl terminus of DUE-B displays amino acid sequence homology to the human ERK5 kinase, and the human androgen receptor, while the amino terminus of DUE-B shows strong homology to an evolutionarily highly conserved domain of unknown function (DUF154).

In *Xenopus oocyte* extracts, baculovirus expressed DUE-B protein associates to form high molecular weight complexes (>250 kDa) while the immuno-crossreactive endogenous frog putative DUE-B protein migrates as ~50 kDa dimers. Similarly, in human cell extracts baculovirus expressed DUE-B protein associates to form high molecular weight complexes (>250 kDa) while the endogenous human DUE-B protein migrates as ~50 kDa dimers. Baculovirus expressed human DUE-B promotes plasmid supercoiling and transiently inhibits DNA replication in these extracts. Restoration of DNA replication may parallel modification of the exogenous DUE-B protein.

Accordingly, it is a feature of the present invention to provide a novel protein which can be used as a target in pharmaceutical assays for chemotherapeutic drugs designed to inhibit tumor cell division, as well as to identify other compounds for enhancing/retarding cell division. This, and other features and advantages of the present invention, will become apparent from the following detailed description and accompanying drawings.

In accordance with the present invention, there is provided a nucleic acid sequence encoding a DNA binding protein involved in DNA replication, said protein comprising an amino acid sequence as set forth in SEQ ID NO:2. In one embodiment, the nucleic acid sequence can be as set forth in SEQ ID NO:1.

In accordance with the present invention, there is also provided a DNA binding protein involved in DNA replication. The protein comprises an amino acid sequence as set forth in SEQ ID NO:2.

In various embodiments, the DNA binding protein described above can be used in a screening method for identifying a compound binding to said amino acid sequence, or in a screening method for identifying a compound modulating the binding of said DNA binding protein to a nucleic acid sequence. The compound preferably screened are those that inhibit cellular proliferation, such as cellular proliferation caused by cancer. Alternatively, the compound that can be screened are those that increase cellular proliferation.

Still in accordance with the present invention, there is also provided an antibody, a derivative or fragment thereof, binding to the DNA binding protein described above and preventing said DNA binding protein from binding to a nucleic acid sequence. The antibody, derivative or fragment thereof, can thus be used for preventing or decreasing cellular proliferation.

Further in accordance with the present invention, there is also provided a gene therapy comprising the step of introducing into a cell an expression vector comprising a nucleic acid sequence encoding a DNA binding protein involved in DNA replication, said protein comprising an amino acid sequence as set forth in SEQ ID NO:2. In one embodiment, the nucleic acid sequence can be as set forth in SEQ ID NO:1, wherein said nucleic acid sequence in said expression vector once introduced in the cell encodes a protein with a DNA binding activity. Preferably, the protein with a DNA binding activity has a sequence as set forth in SEQ ID NO:2.

Also in accordance with the present invention, there is provided a method for screening compounds capable of modulating amino acids-DNA interaction, said method comprising the steps of:

a) contacting in a medium the DNA binding protein described above the a DNA, said DNA binding protein being detectable and binding to said DNA;

b) adding to said medium) a compound to be screened for its capacity to modulate the binding of amino acids to said DNA; and c) detecting the effect on binding of the DNA binding protein to the DNA by the compound to be screened.

The present invention also provides a method for screening compounds capable of modulating DNA replication, said method comprising the steps of:

a) contacting in a medium a compound to be screened with a DNA binding protein comprising an amino acid sequence as set forth in SEQ ID NO:2; and b) determining binding of said compound to the DNA binding protein, wherein detection of binding is indicative that said compound is capable of modulating DNA replication.

The present invention further provides a method for screening compounds capable of modulating DNA replication, said method comprising the steps of:

a) contacting in a medium a compound to be screened with a DNA binding protein comprising an amino acid sequence as set forth in SEQ ID NO:2; and b) determining binding of said compound to the DNA binding protein, wherein detection of binding is indicative that said compound is capable of modulating DNA replication.

In accordance with the present invention, there is also provided a method for screening compounds capable of modulating cell proliferation, said method comprising the steps of:

a) contacting in a medium a compound to be screened with a DNA binding protein comprising an amino acid sequence as set forth in SEQ ID NO:2; and b) determining binding of said compound to the DNA binding protein, wherein detection of binding is indicative that said compound is capable of modulating cell proliferation.

In accordance with the present invention, there is additionally provided a method for screening compounds capable of modulating proliferation, said method comprising the steps of:

a) contacting in a medium a compound to be screened with a DNA binding protein comprising an amino acid sequence as set forth in SEQ ID NO:2;

b) adding DNA to said medium; and c) determining binding of said compound to the DNA binding protein, wherein detection of the binding is indicative that said compound is capable of modulating cell proliferation.

BRIEF DESCRIPTION OF THE DRAWINGS

The following detailed description will be more fully understood in view of the drawings in which:

FIG. 3 is an illustration of the DUE-B cDNA (SEQ ID NO:1) and protein (SEQ ID NO:2) sequences;

FIGS. 20A to 20D illustrate the interaction of DUE-B with chromatin;

Figure 1:
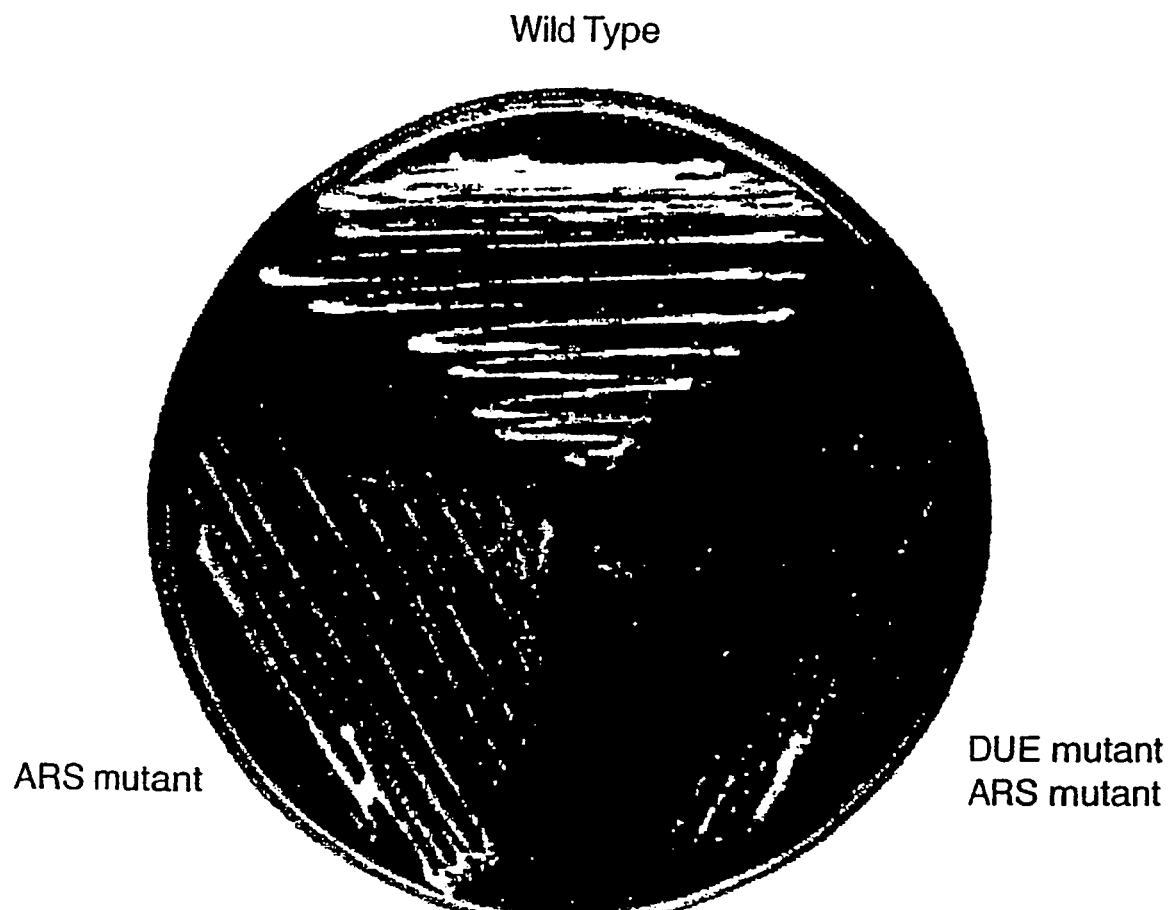
FIG. 1 is a photograph showing the Yeast One-Hybrid Assay.

The embodiments set forth in the drawings are illustrative in nature and are not intended to be limiting of the invention defined by the claims. Moreover, individual features of the drawings and the invention will be more fully apparent and understood in view of the detailed description.

DETAILED DESCRIPTION

In the figures and throughout the application, references are made to specific compounds by a numeral reference. Table 1 below provides the correspondence between the numeral reference and the actual compounds.

TABLE 1

LIST OF COMPOUNDS USED AND/OR TESTED

| Steroid number (from Steraloids) | Steroid name [TRIVIAL (IUPAC)] |
| --- | --- |
| P650 | 1-DEHYDROCORTISOL, PREDNISOLONE (1,4-pregnadien-11b,17,21-triol-3,20-dione) |
| E870 | 17a-ESTRADIOL (1,3,5(10)-estratriene-3,17a-diol) |
| E950 | 17b-ESTRADIOL [1,3,5(10)-estrien-3,17-diol-17-acetate] |
| E952 | 17b-ESTRADIOL 17-ACETATE [1,3,5(10)-estratriene-3,17b-diol] |
| E1130 | 2-HYDROXYESTRONE [1,3,5(10)-estratrien-2,3-diol-17-one] |
| E1140 | 2-METHOXYESTRONE 3-METHYL ETHER [1,3,5(10)-estratrien-2,3-diol-17-one 2,3-dimethyl ether] |
| E1250 | 16a-HYDROXYESTRONE [1,3,5(10)-estratrien-3,16a-diol-17-one] |
| E1400 | 16-KETO-17b-ESTRADIOL [1,3,5(10)-estratrien-3,17b-diol-16-one] |
| E2300 | ESTRONE [1,3,5(10)-estratrien-3-ol-17-one] |
| E2301 | ESTRONE ACETATE [1,3,5(10)-estratrien-3-ol-17-one acetate] |

TABLE 1-continued

LIST OF COMPOUNDS USED AND/OR TESTED

| Steroid number (from Steraloids) | Steroid name [TRIVIAL (IUPAC)] |
| --- | --- |
| E2470 | 2-HYDROXYESTRADIOL [1,3,5(10)-estratrien-2,3,17b-triol] |
| E2500 | 4-HYDROXYESTRADIOL [1,3,5(10)-estratrien-3,4,17b-triol] |
| E2600 | ESTRIOL [1,3,5(10)-estratriene-3,16a,17b-triol] |
| E2602 | ESTRIOL 16-ACETATE [1,3,5(10)-estratrien-3,16a,17b-triol 16-acetate] |
| E2695 | ESTRIOL 3-HEMISUCCINATE [1,3,5(10)-estratrien-3,16a,17b-triol 3-hemisuccinate] |
| E2696 | ESTRIOL 16-HEMISUCCINATE [1,3,5(10)-estratrien-3,16a,17b-triol 16-hemisuccinate] |
| E2750 | ESTRIOL TRIACETATE [1,3,5(10)-ESTRATRIEN-3,16α,17β-TRIOL TRIACETATE] |
| E2800 | 16,17-EPIESTRIOL [1,3,5(10)-estratrien-3,16,17-triol] |
| E2850 | 16-EPIESTRIOL [1,3,5(10)-estratrien-3,16,17-triol] |
| Q2600 | PROGESTERONE [4-pregnene-3,20-dione] |
| Q3880 | HYDROCORTISONE (4-pregnen-11b,17,21-triol-3,20-dione) |
| A6950 | TESTOSTERONE [4-androsten-17b-ol-3-one] |

Replication of the genome is essential for cell division and is regulated so that the entire DNA is duplicated once during the cell cycle. To accomplish the exact duplication of the genome, eukaryotic cells regulate where replication initiates along the chromosome, and when replication begins during the cell division cycle. Mutations in these controls can lead to chromosome instability, cancer, or cell death (Hartwell, L. H., and M. B. Kastan, Science 266:1821-8, 1994).

The sites where the initiation of replication is controlled are termed replication origins. In *S. cerevisiae*, chromosomal replication origins cloned in plasmids display autonomous replicating sequence (ARS) activity, and characteristically comprise a set of modular elements including an ARS consensus sequence (ACS) binding site for the yeast initiator protein, the origin recognition complex (ORC) (Newlon, C. S., and J. F. Theis, *Curr. Opin. Genet. Dev.* 3:752-758, 1993). Other origin components include a region of helical instability termed a DNA unwinding element (DUE), and transcription factor binding sites that may promote the assembly of replication complexes through protein-protein interactions and modulations of chromatin structure. In mammalian nuclei no consensus DNA sequence has been identified that is analogous to the yeast initiator protein binding site (Cimbora, D. M., and M. Groudine, *Cell* 104:643-646, 2001). Instead the feature most common to mammalian origins is not a DNA sequence but a structure, the DNA unwinding element, DUE (Dobbs, D. L., et al., *Nucleic Acids Res.* 22:2479-2489, 1994).

A replication origin in the 5' flanking region of the human c-myc gene was first identified in the laboratory of one of the inventors (Leffak, M., and C. D. James, *Mol. Cell. Biol.* 9:586-593, 1989; McWhinney, C., and M. Leffak, *Nucleic Acids Res.* 18:1233-1242, 1990; and McWhinney, C., and M. Leffak, 1988. Episomal persistence of a plasmid containing human c-myc DNA, vol. 6. CSH Laboratory Press, New York.). Subsequently this conclusion was confirmed by Vassilev and Johnson by PCR mapping of DNA nascent strands, and by others (Phi-van, L., et al., *J. Biol. Chem.* 273:18300-

18307, 1998; Rein, T., et al., *J. Biol. Chem.* 274:25792-80025, 1999; Tao, L., et al., *J. Cell. Biochem.* 78:442-457, 2000; Tao, L., et al., *J. Mol. Biol.* 273:509-518, 1197; and Vassilev, L., and E. M. Johnson, *Mol. Cell. Biol.* 10:4899-4904, 1990). The inventors have also shown that the c-myc 2.4 kb HindIII/Xhol fragment endows the plasmid pNeo-.Myc-2.4 with autonomously replicating sequence (ARS) activity when transfected into HeLa cells, and in human cell free extracts in vitro (Berberich, S., A., et al., *J. Mol. Biol.* 245:92-109, 1995; Malott, M., and M. Leffak, *Mol. Cell. Biol.* 19:5685-5695, 1999; McWhinney, C., and M. Leffak, *Nucleic Acids Res.* 18:1233-1242, 1990; McWhinney, C., and M. Leffak, 1988, Episomal persistence of a plasmid containing human c-myc DNA, vol. 6. CSH Laboratory Press, New York; McWhinney, C., et al., *DNA Cell Biol.* 14:565-579, 1995; Trivedi, A., et al., *DNA Cell Biol.* 17:885-896, 1998). Replication in vitro initiates in the c-myc insert of the plasmid as demonstrated by two dimensional electrophoresis, electron microscopy and nascent strand polarity mapping and closely corresponds to the c-myc initiation zone deduced by Ishimi et al. (Ishimi, Y., et al., *Mol. Cell. Biol.* 14:6489-6496, 1994).

Computer analysis of the nucleotide sequence in the 5' flanking DNA of the human c-myc gene predicted several regions of inherently bent or rigid DNA. These predictions were confirmed by two dimensional gel electrophoresis of c-myc restriction fragments. Nuclease digestion revealed a series of positioned nucleosomes and nuclease hypersensitive sites in the 2.4 kb region upstream of the c-myc promoters (Kumar, S., and M. Leffak, *J. Mol. Biol.* 222:45-57, 1991; and Kumar, S., and M. Leffak, *Nucleic Acids Res.* 17:2819-2833, 1989).

This unique chromatin arrangement was stable when the 2.4 kb Hindlll/Xhol fragment containing the c-myc ARS element was translocated to other regions of the HeLa genome in an adeno-associated virus/c-myc construct, indicating that the structure is established by the bending or other sequence-directed features of the DNA. Several transcription factor consensus binding sites are present in the 5' flanking region of the human c-myc gene (Michelotti, G. A., et al., *Mol. Cell. Biol.* 16:2656-2669, 1995). One of these, a CTF/NF1 binding site, is close to DNase hypersensitive site II1 and a predicted DUE whose calculated free energy cost of unwinding is comparable to those of functional ARS elements in *S. cerevisiae*. The DUE is inside a region of ~100 bp that contains three 10/11 matches to the *S. cerevisiae* ARS consensus sequence. Comparison of the amino acid expressed by DUE with sequences on NCBI resulted in an almost perfect match with a predicted protein from a *Homo sapiens* histidyl-tRNA synthetase mRNA posted by Mao et al. (AF332356). However, Moa et al. never suggested that the predicted protein would have DNA binding properties. The DUE/ARS region spans the c-myc far upstream element (FUSE) which is $KMnO_4$ reactive in HeLa cells and is likely stabilized in an unwound state by interaction with the FUSE-binding protein FBP (Bazar, L., et al., *J. Biol. Chem.* 270:8241-8248, 1995; Duncan, R., et al., *Genes Dev.* 8:465480, 1994; Michelotti, G. A., et al., *Mol. Cell. Biol.* 16:2656-2669, 1996).

Mapping of DNA nascent strands confirmed that replication initiates at multiple sites within and flanking the 2.4 kb c-myc core origin at its endogenous location. To test whether this region satisfies the genetic definition of a chromosomal replicator which is able to promote its own replication and that of flanking chromosomal sequences, the core c-myc origin, or control DNA, was integrated at the same ectopic chromosomal site in human cells using the *S. cerevisiae* FLP recombinase enzyme (Malott, M., and M. Leffak, *Mol. Cell. Biol.* 19:5685-5695, 1999). The abundance of short nascent DNA strands at the chromosomal acceptor site was quantitated before and after targeted integration of the origin fragment and showed that the c-myc origin DNA substantially increased the amount of nascent DNA relative to the level at the unoccupied acceptor site, and when compared to the level of nascent strands after insertion of control DNA. These results provided biochemical and genetic evidence for the replicator activity of the 2.4 kb region of c-myc origin DNA.

The same system was used to demonstrate that removal of the DUE/ARS region decreased c-myc chromosomal origin activity by more than half. Thus, the DUE/ARS is an essential component of the mammalian c-myc origin, as it is in yeast origins. To identify proteins that might regulate origin activity by binding to the DUE, a yeast one hybrid assay was used. The present application describes the identification and characterization of a novel HeLa protein, DUE-B, which binds specifically to the c-myc DUE in vivo.

Results

Figure 2:
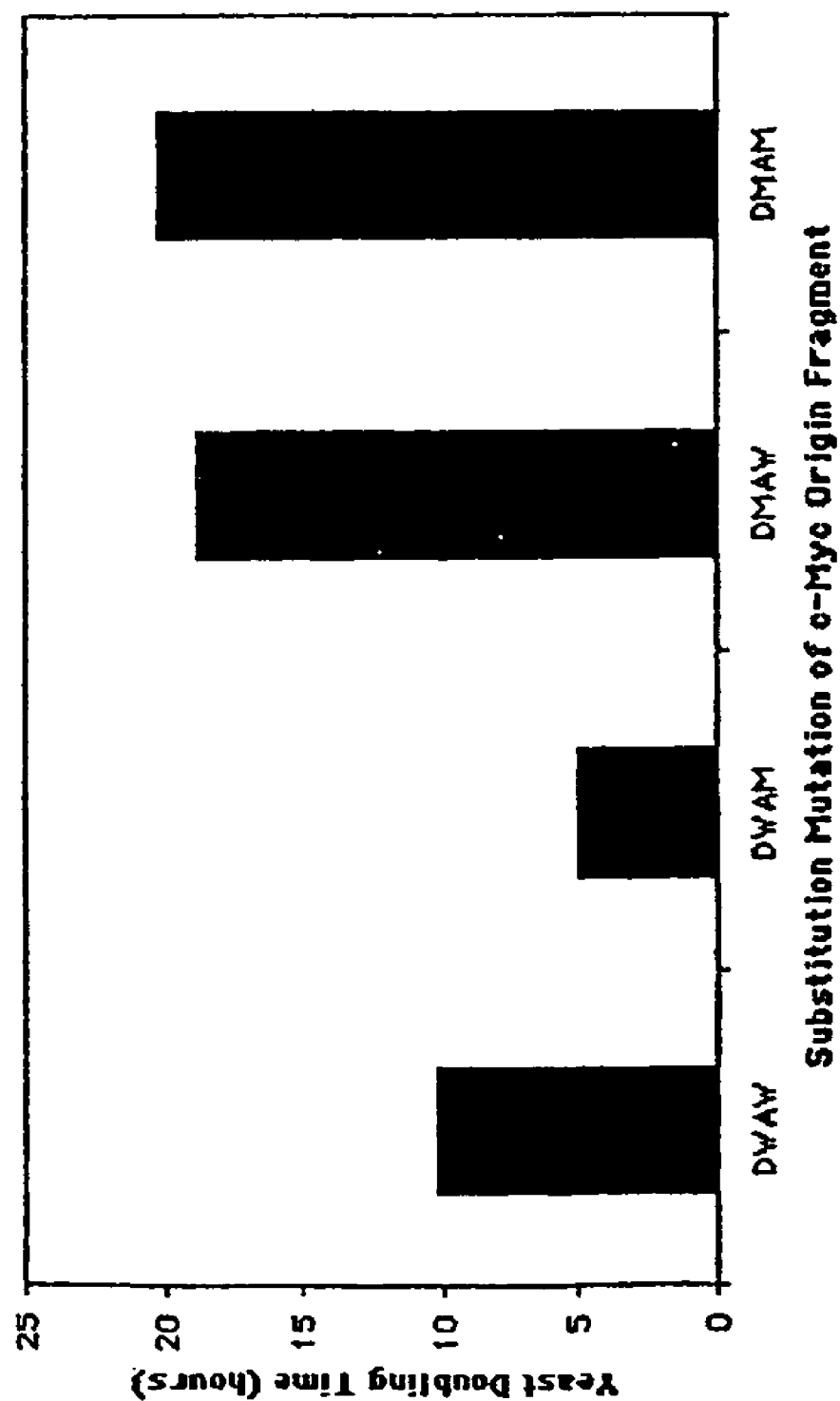
FIG. 2 shows the target sequence effects on DUE-B binding.

The DNA unwinding element and ARS flanking DNA (102 bp) of the human c-myc gene was used as a bait sequence to isolate cognate sequence-specific or structure-specific binding proteins in a yeast one-hybrid screen. The DUE/ARS was cloned upstream of a His3 reporter gene promoter and integrated into a his-*S cerevisiae* strain. Due to low level, leaky expression of the bait construct stable integration of the reporter could be selected for on his-plates. The reporter yeast strain was transfected with a HeLa cDNA library (>$10^6$ cDNA cfu) cloned in the pGAD-GH vector, to produce fusion proteins containing the Gal4 transcription activation domain and HeLa proteins. Transfected yeast were selected for plasmid retention (leu+) and elevated expression of the His3 reporter in the presence of 3-aminotriazole. One cDNA, pGK16B, resulted in large colony growth under selective conditions (FIG. 1). In FIG. 1, reporter yeast containing a histidine reporter gene (HIS3) downstream of the wild type c-myc DUE/ARS element, wild type DUE/mutant ARS element, or mutant DUE/mutant ARS element were transformed with the pGK16B plasmid (encoding the DUE-B protein) and grown on his-medium with the histidine anti-metabolite 3-AT (5 mM). The presence of DUE-B promotes the expression of His3 reporter gene and yeast growth only in cells containing the wild type DNA binding site for DUE-B. Similar relative growth rates for the three types of transformants were observed on his-medium with 0, 5, 10, or 15 mM 3-AT. FIG. 2 illustrates the growth rates in liquid culture (+5 mM 3-AT) of the yeast reporter strains containing the wild type c-myc DUE/ARS element (DWAW), wild type DUE/mutant ARS element (DWAM), mutant DUE/wild type ARS element (DMAW) or mutant DUE/mutant ARS element (DMAM). It is to be noted that mutation of the ARS consensus site for ORC binding enhances the effect of DUE-B binding (increased growth rate), while mutation of the DUE slows growth. This data shows that the unwinding element is critical for the activation of the c-myc ARS.

Isolation of pGK16B and retransformation into the original reporter strain (DUE/ARS WT) resulted in robust colony growth. Transformation of pGK16B into otherwise isogenic yeast containing point substitutions in the ARS Sequences slightly suppressed growth, while pGK16B could not sustain growth of otherwise isogenic yeast containing substitutions in the ARS and DUE of the reporter. The protein encoded by pGK16B therefore binds to the wild type DUE/ARS and enables the Gal4 transcription activator to activate expression of the His3 reporter. In contrast, mutation of the ARS region of the DUE/ARS bait decreased reporter expression, suggesting that the endogenous yeast replication initiator complex ORC may interact with DUE-B during DNA binding. Mutation of the DUE and ARS elements eliminated reporter gene expression, indicating that the DUE region of the bait is essential for DUE-B binding. The pGK16B cDNA was therefore renamed DUE-B to denote its affinity for DUE binding in vivo.

Sequencing of the DUE-B cDNA revealed an open reading frame of 209 amino acids (FIG. 3). DUE-B amino acids 29-147 are strongly (>90%) homologous to a domain of unknown function (DUF154) evolutionarily conserved in bacteria, yeast, and mammals. C-terminal to the DUF154 homology is a coiled-coiled domain characteristic of protein interaction sites, followed by a region of C-terminal homology (>50%) to segments of the human androgen receptor protein and to the ERK5 nuclear MAP kinase. The DUE-B gene spans seven exons on chromosome 20, with the proposed initiator methionine located in exon 2. In FIG. 3, the DUE-B cDNA sequence from the pGK16B plasmid is shown. Below is the one letter amino acid translation of the sequence. A protein of 209 amino acids is predicted. The putative initiator methionine ATG occurs in exon 2. Black/grey underlines indicate successive exons. The asterisk in exon 7 indicates the putative stop codon.

Figure 4A:
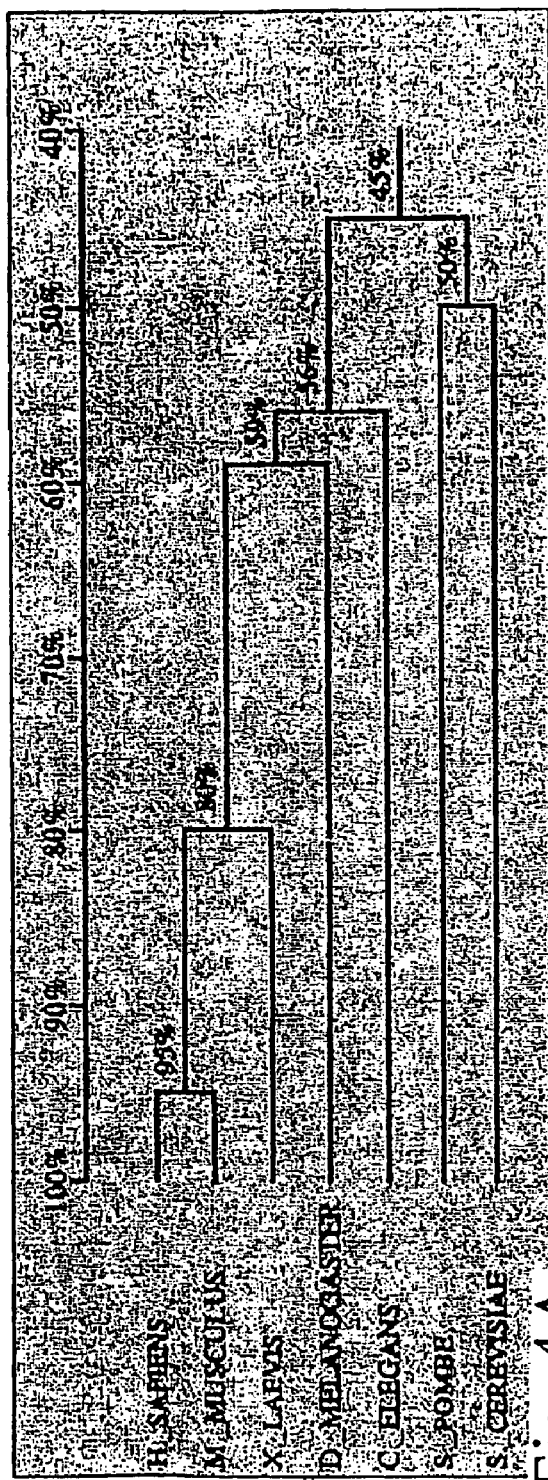
FIGS. 4A and 4B show the degree of homology between DUE-B from humans and other organisms, in the form of an evolutionary tree (FIG. 4A) and percent identity indicated on the chart at the bottom (FIG. 4B)
Figure 4B:

As can be seen from FIGS. 4A and 4B, the degree of conservation between human and yeast sequences (45%) indicates the presence of some essential regions of the protein.

Figure 5A:
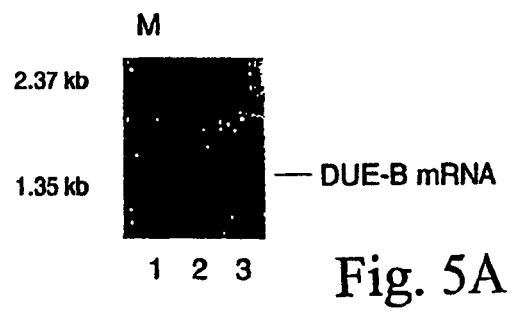
FIGS. 5A and 5B are photographs showing mRNA and protein expression.

Northern blot analysis revealed a single species of 1.35 kb DUE-B mRNA (FIG. 5A). FIG. 5A reports Northern blot analysis of HeLa RNA probed with DUE-B cDNA. Lane 1 of FIG. 5A has been loaded with cross-hybridizing size marker RNA, whereas lanes 2 and 3, were loaded with HeLa RNA.

Figure 5B:
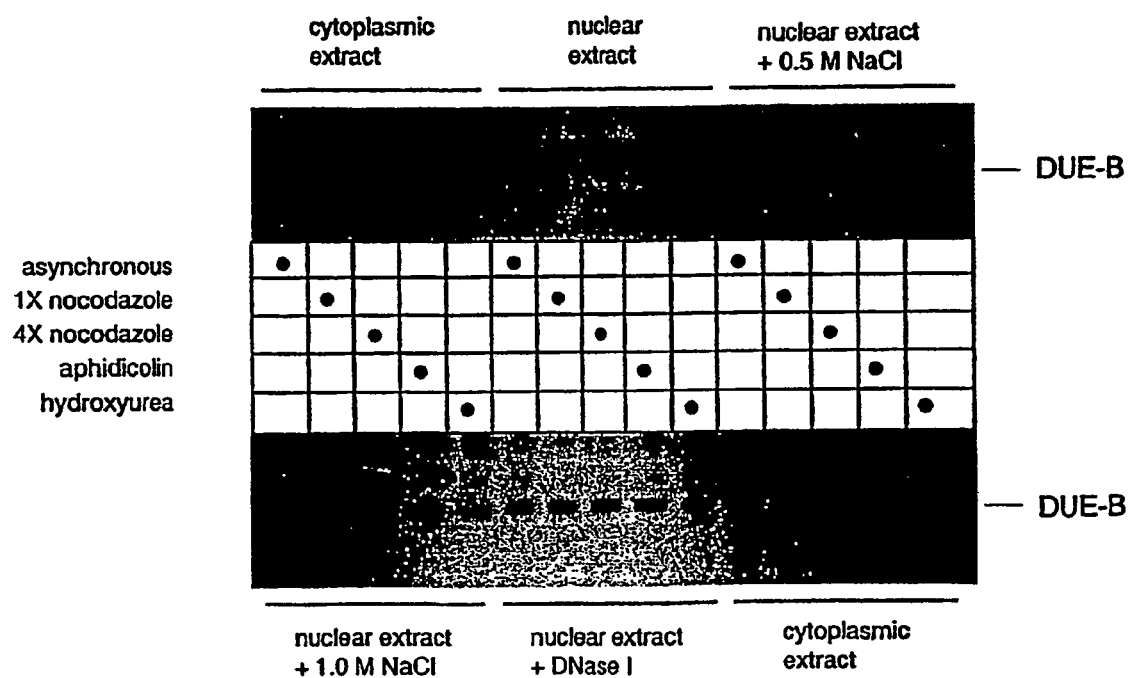
Figure 6:
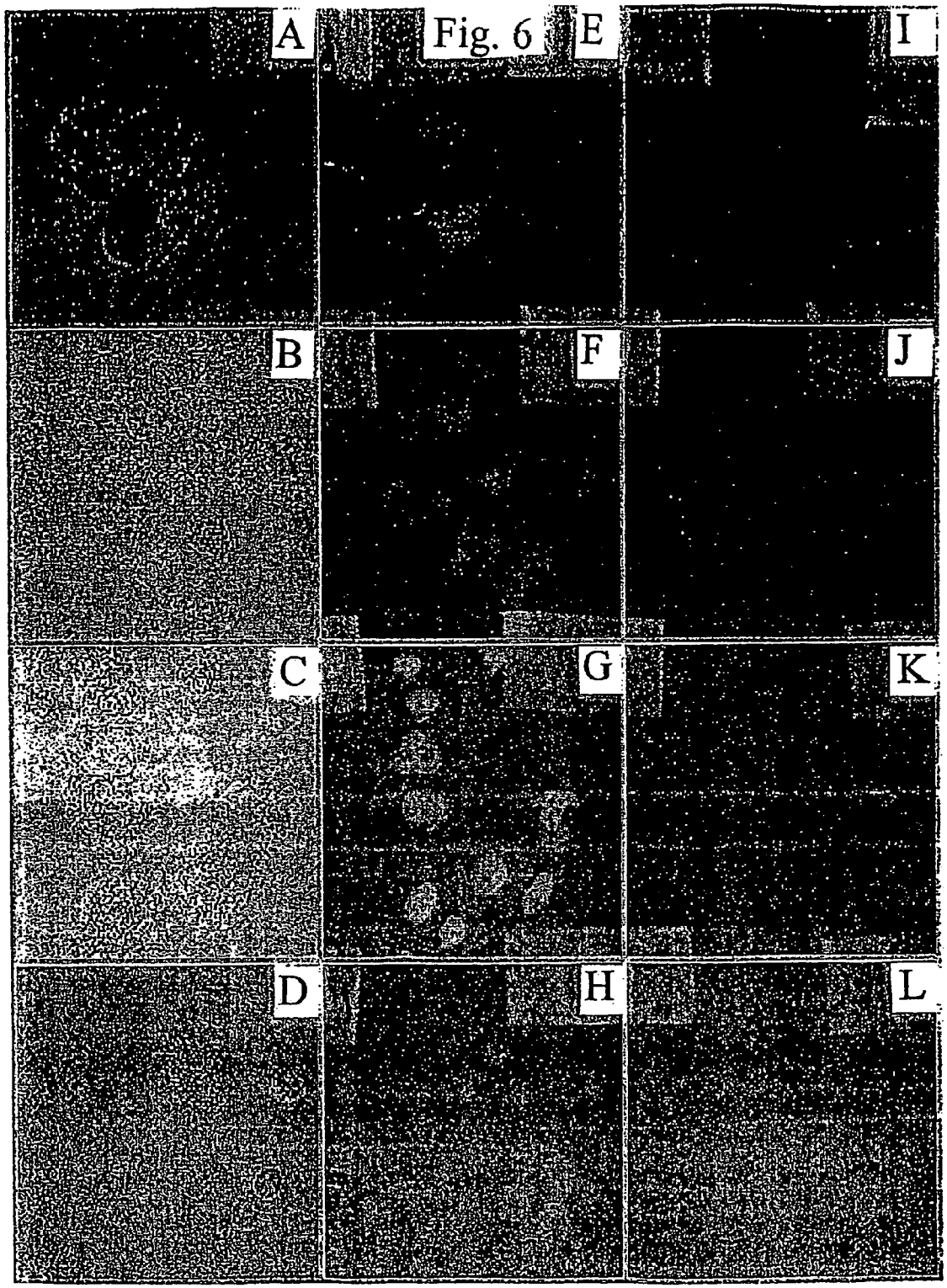
FIGS. 6A to 6L illustrate photographs showing immunocytochemistry of HeLa cells expressing 6his, V5 epitope-tagged DUE-B, visualized in the cell nuclei by phase contrast microscopy (FIGS. 6A to 6D), Hoechst staining (FIGS. 6E to 6H), and FITC-conjugated V5 monoclonal antibody (FIGS. 6I to 6L)

DUE-B was cloned into the pTRC-His vector and expressed in $E.$ $coli$. The protein was purified by nickel column chromatography and used to prepare polyclonal antibody. Western blot analyses showed that approximately 75% of DUE-B protein is found in the cytoplasmic fraction when cells are lysed in mild detergent (FIG. 5B). In FIG. 5B, proteins from nuclear or cytoplasmic extracts were separated by SDS-PAGE and western blots were probed with a polyclonal anti-DUE-B antibody. The nuclear fraction of DUE-B can be extracted with moderate to high salt (0.5-1.0 M NaCl) and by DNase1 digestion, indicating that the nuclear fraction of DUE-B is bound to DNA. The intracellular distribution of DUE-B observed in asynchronous cells did not change when cells were arrested in mitosis with nocodazole, or in S phase with aphidicolin or hydroxyurea. These results were consistent with the observation that the level of DUE-B mRNA did not change appreciably over the course of the cell cycle.

To assess the distribution of DUE-B in intact cells an epitope tagged (V5, myc tags) version of the protein was expressed in HeLa cells. Immunocytochemical analysis using anti-myc antibody (FIGS. 6I to 6L) or anti-V5 antibody revealed that the expressed protein was localized to the nucleus. In contrast, control reactions using the same antibodies to monitor the distribution of a V5, his6-tagged MDM2 protein displayed only the expected cytoplasmic fluorescence. These observations show that DUE-B is located in the nucleus in intact HeLa cells.

Figure 7:
FIG. 7 illustrates photographs showing the distribution of DUE-B in the nuclei and the supernatant.

In FIG. 7, it is shown that DUE-B is released into the supernatant (S) from pelleted (P) HeLa nuclei by micrococcal nuclease digestion (lanes 5, 6) or HaeIII restriction DNase digestion (7,8). A small amount of DUE-B is released from nuclei in the presence of RNase (lanes 3, 4), similar to the amount of DUE-B released by incubation at 37° C. in the absence of exogenous nuclease (lanes 1, 2). Thus, DUE-B appears to be specifically bound to chromatin in nuclei.

Figure 8:
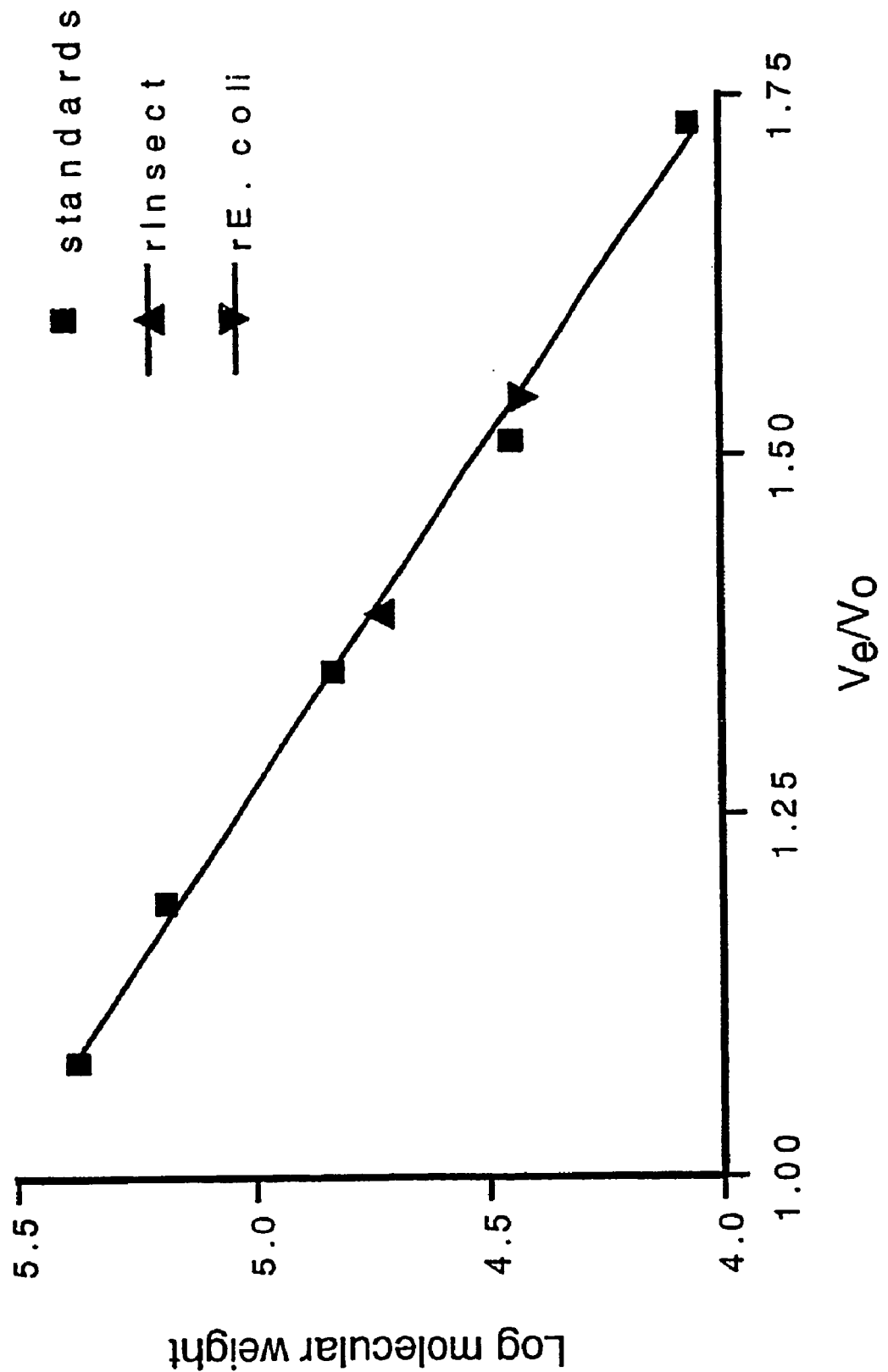
FIG. 8 is a plot diagram of Sephacryl™ S-200 HR gel filtration of recombinant DUE-B.
Figure 9:
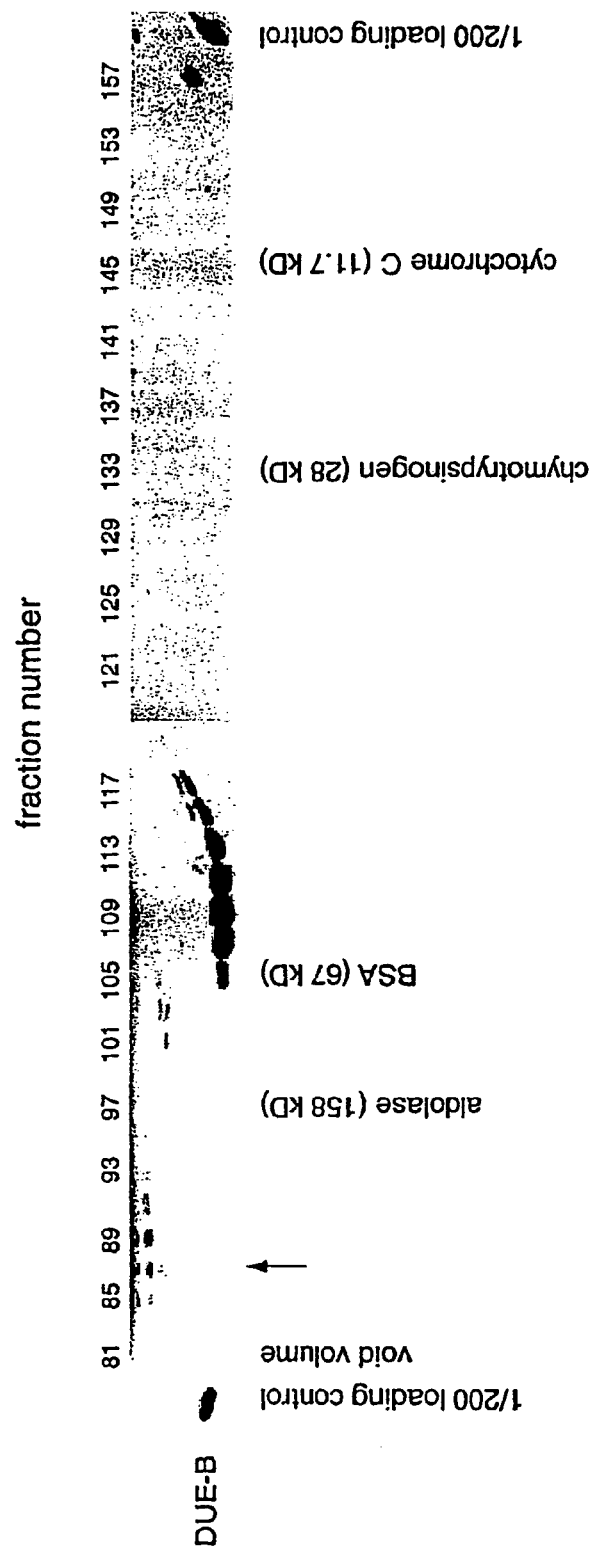
FIG. 9 is a photograph showing the results of HeLa whole cell extract chromatographed on Sephacryl™ S-200 HR as in FIG. 8.

The presence of a coiled-coil domain in the protein implied that DUE-B might form homo- or heteromeric complexes. The elution profile of the bacterial expressed DUE-B protein on Sephacryl™ S-200 column chromatography was consistent with its monomeric molecular weight of 26 kDa (FIG. 8). In FIG. 8, a Sephacryl™ S-200 column was calibrated using catalase, aldolase, BSA, chymotrypsinogen and cytochrome C. A calibration curve was generated to determine the molecular weight of DUE-B recombinant proteins (c-myc, 6his epitope tagged) produced in $E.$ $coli$ and SF9 insect cells. The elution peaks of the recombinant proteins were determined by ELISA. A monoclonal antibody against the c-myc epitope was used to assay the rGK16B produced in $E.$ $coli$. Polyclonal rabbit antibody against DUE-B expressed in $E.$ $coli$ was used to assay the DUE-B produced in insect cells. One major peak was observed in each ELISA. The $E.$ $coli$ generated protein has an apparent molecular weight of 26.4 kDa (monomeric) while the insect expressed protein has an apparent molecular weight of 54.7 kDa. In contrast, when DUE-B was purified from insect cells infected with recombinant baculovirus, the recombinant DUE-B eluted as a dimer, near 50 kDa. Thus, expression in eukaryotic cells may enhance DUE-B protein-protein interaction by alteration in protein folding or other posttranslational modifications. To determine whether DUE-B existed in monomeric or multimeric states in HeLa cells, cell extracts were chromatographed. As seen in FIG. 9, endogenous DUE-B eluted at a molecular weight corresponding to ca 50-54 kDa, with a small percentage of the protein eluting near the void volume (fraction 87; 250 kDa). In FIG. 9, fractions were separated by SDS-PAGE and visualized by western blotting with the anti-DUE-B antibody.

Figures 10A, 10B:
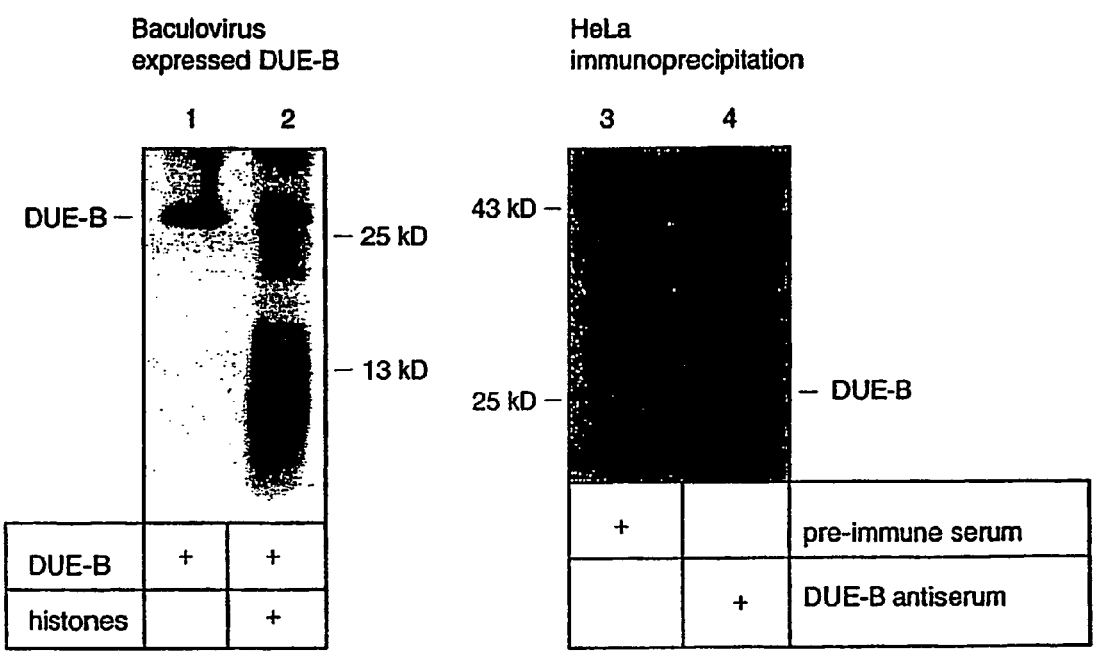
FIGS. 10A and 10B are photographs showing in vitro phosphorylation.

A crude preparation of his-tagged DUE-B expressed in a baculovirus vector and purified on a nickel affinity column displayed ATPase activity and the ability to be phosphorylated in vitro with gamma-$^{32}$P-ATP in the absence (lane 1) or presence (lane 2) of histones (FIG. 10A). Similarly, DUE-B immunoprecipitated with preimmune serum (lane 3) or DUE-B antiserum (lane 4) from HeLa cell extracts also copurified with kinase activity and could be phosphorylated with gamma-$^{32}$P-ATP (FIG. 10B). However, immunoprecipitation of cell extracts labeled in vivo with $^{32}$P-phosphoric acid did not reveal a significant level of DUE-B phosphorylation. Thus, DUE-B may be transiently phosphorylated or unphosphorylated in vivo.

Figure 11:
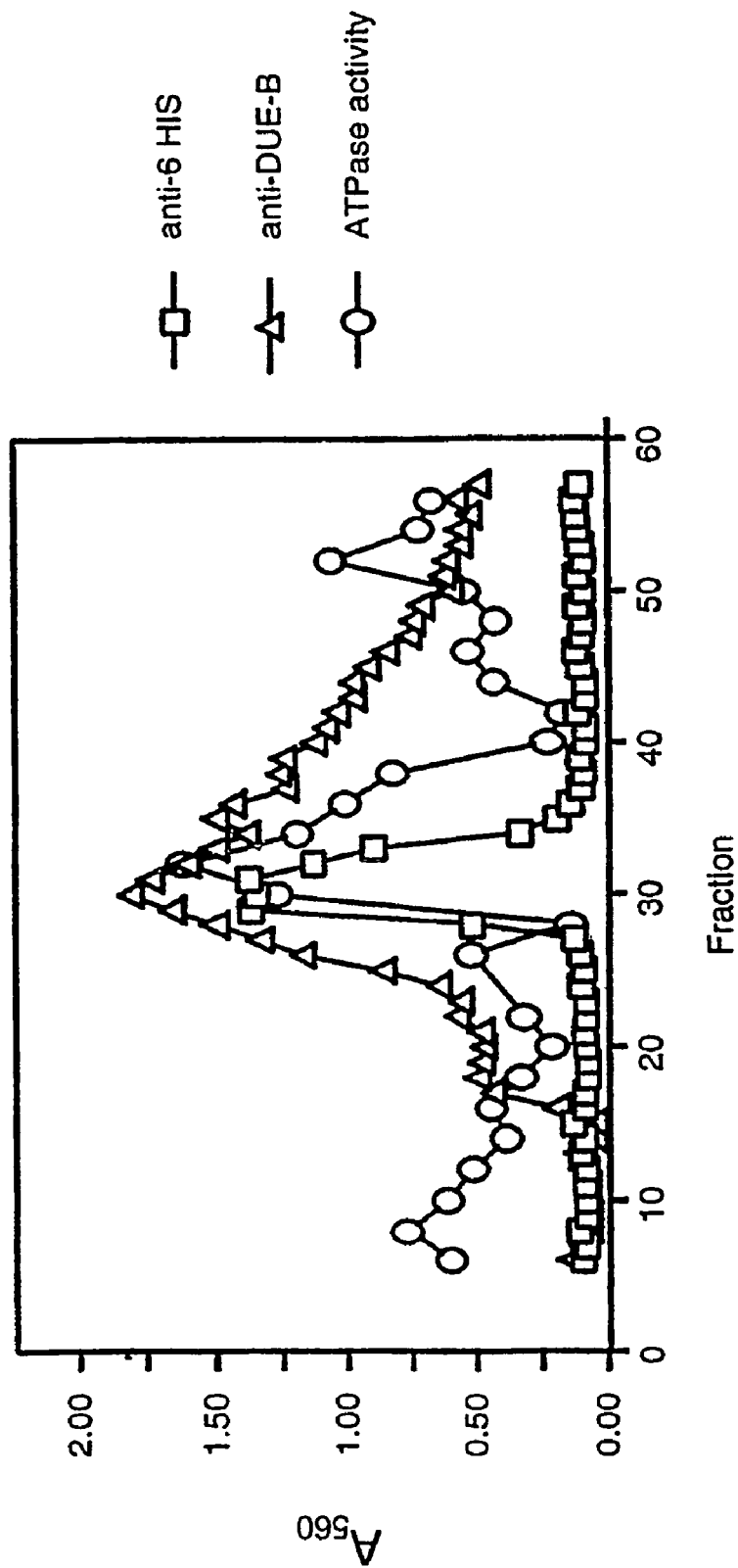
FIG. 11 is a plot diagram of ATPase chromatography.
Figure 12:
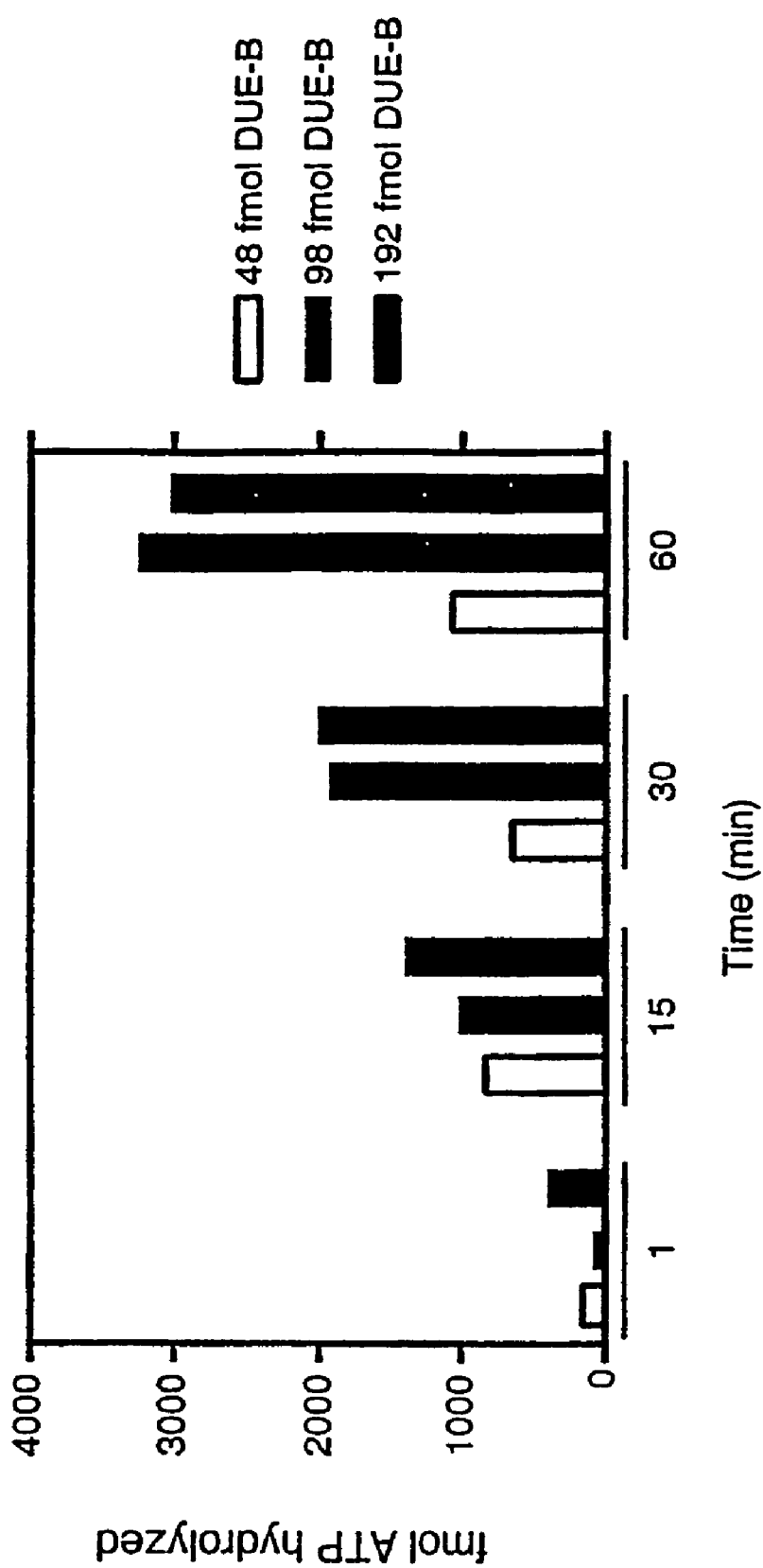
FIG. 12 is a graph of the quantification of ATPase activity present in DUE-B.

Column chromatography revealed that the kinase activity associated with the baculovirus expressed DUE-B was not an inherent activity in the protein, fractionating from the immunoreactive DUE-B in early and late eluting peaks (FIG. 8). In FIG. 11, DUE-B expressed in baculovirus infected insect cells was chromatographed as in FIG. 8. To locate the eluted DUE-B, fractions were assayed by ELISA using DUE-B antibody or 6his antibody. ATPase activity was monitored by thin layer chromatography of alternate fractions incubated with gamma-$^{32}$P-ATP. However, the ATPase activity co-eluted with the DUE-B immunoreactive material, indicating that the DUE-B protein possesses intrinsic ATPase activity. Quantitation of the DUE-B ATPase activity by thin layer chromatography showed that approximately 30 fmol gamma-$^{32}$P-ATP were hydrolyzed per hour per fmol of DUE-B (FIG. 12). In FIG. 12, time courses of ATPase activity were measured for three concentrations of DUE-B protein.

Figure 13:
FIG. 13 is a photograph showing that DUE-B and Replication Protein A (RPA) cooperate to affect DNA topology.

On a chloroquine agarose gel of plasmid DNA, changes in the distribution of bands a, b, c, d in FIG. 13 indicate that DUE-B plus RPA increases plasmid supercoiling by 1-2 turns more than either protein alone (compare lanes 3, 4, 5) and this effect is potentiated by ATP (compare lanes 8, 10, 11 with 3, 4, 5).

Figure 14:
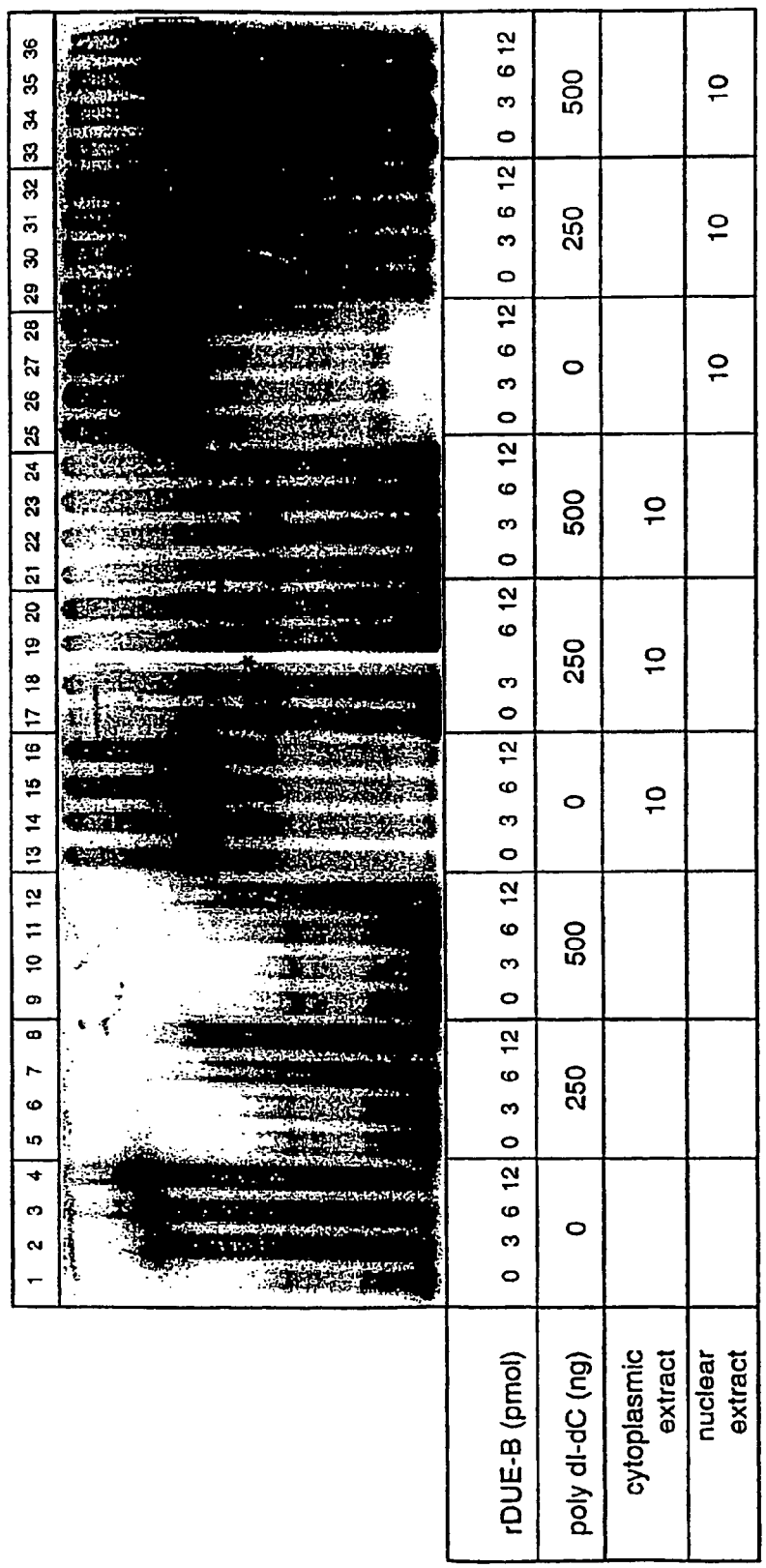
FIG. 14 illustrates an electrophoretic mobility shift analysis (EMSA)

An electrophoretic mobility shift assay (EMSA) was used to test whether the baculovirus expressed DUE-B protein could bind to DNA in vitro. When added to a radiolabeled c-myc DUE probe in the absence of nonspecific competitor (poly dI-dC), DUE-B produced a strongly retarded protein-DNA complex band (FIG. 14, lanes 1-4). Increasing the concentration of poly dI-dC (lanes 5-12) reduced the levels of DUE-B bound DNA, suggesting that DUE-B can bind DNA nonspecifically. When HeLa cell cytoplasmic extract was added to the c-myc DUE probe in the absence of poly dI-dC an intense band was observed that was not affected by the addition of DUE-B (lanes 13-16). With the addition of the nonspecific competitor poly dI-dC, however, a novel band appeared that was dependent on the addition of DUE-B (asterisks, lanes 17-24). These results indicate that DUE-B interacts with proteins released in the HeLa cytosol to form a specific complex on DNA. Similar to the results obtained when cytosol was added to the c-myc DUE probe, when nuclear extract from HeLa cells was added to the c-myc DUE probe in the absence of poly dI-dC an intense band was observed that was not affected by the addition of DUE-B (lanes 25-28). In the presence of competitor for nonspecific binding, however, a novel band appeared that was dependent on the addition of DUE-B (brackets, lanes 32 and 36). These results indicate that DUE-B interacts with HeLa nuclear proteins to form specific complexes on the c-myc origin DNA. In FIG. 14, a 123 bp fragment of the c-myc replication origin containing the DUE/ARS region was labeled with alpha-$^{32}$P-dCTP by PCR. 25 fmol were mixed with recombinant DUE-B purified by Ni-NTA affinity chromatography from SF9 insect cells. EMSAs were performed in the presence of an inhibitor of non-specific DNA binding, poly dI-dC, HeLa cytoplasmic extract or HeLa nuclear extract as indicated. The labeled origin DNA was visualized by autoradiography. The data show that purified DUE-B protein alters the electrophoretic migration pattern of origin DNA bound by HeLa proteins.

Figure 15:
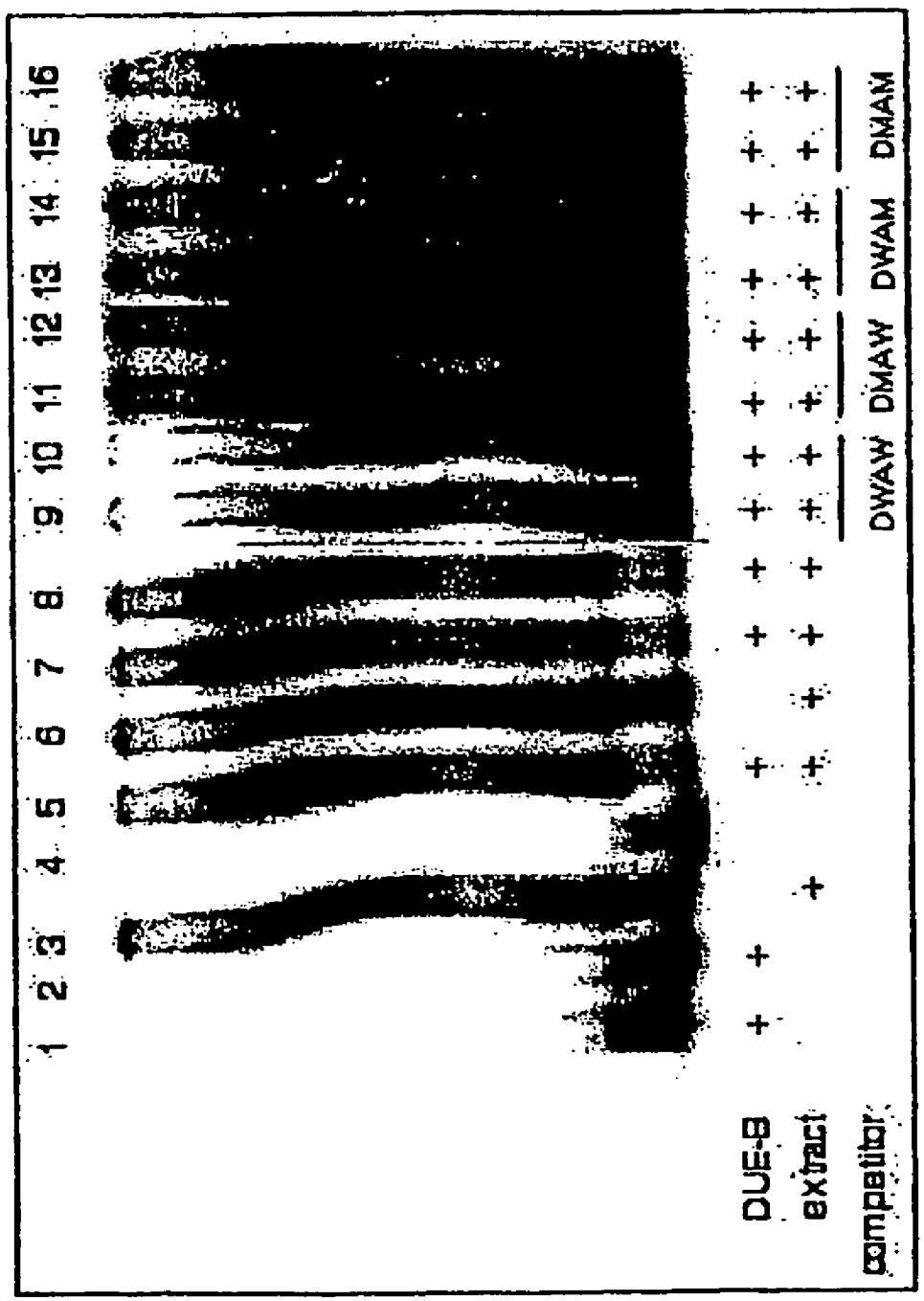
FIG. 15 shows electrophoretic mobility shift assays using DUE-B and HeLa nuclear extract bound to a DUE/ARS probe in the presence of poly-dI-dC and the indicated competitors.

In FIG. 15, competition EMSA reveals the sequence-selective binding of DUE-B: protein complexes. DUE-B changes the binding pattern of HeLa nuclear extract proteins (compare lanes 3, 6 with 5, 7 and 8). Note also the competition for DUE-B: protein complex binding to the probe by DWAW but not mutant DUE/ARS sequences DMAW, DWAM, DMAM.

Figure 16:
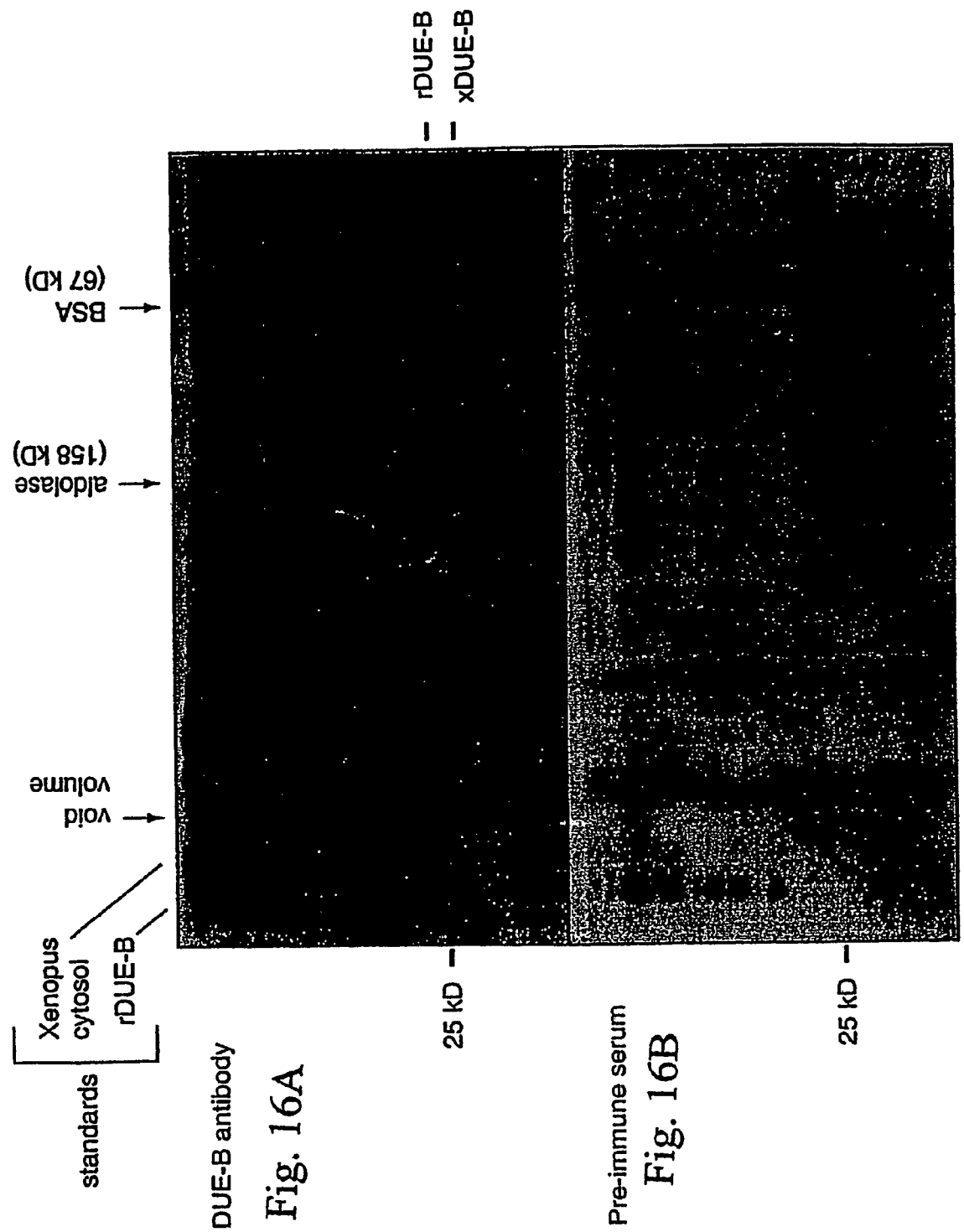
FIGS. 16A and 16B are photographs showing chromatography of DUE-B in *Xenopus oocyte* extract.

As shown during the chromatography of HeLa extracts, virtually all of the endogenous DUE-B protein migrates as a dimer of ca. 50 kDa during gel exclusion, although a minute amount of the protein can reproducibly be detected at a substantially higher molecular weight (FIG. 9, fraction 87, arrow). Since it can be estimated that fewer than 10% of asynchronously dividing HeLa cells are in that portion of the cell cycle when pre-replicative complexes are assembled we sought for DUE-B interacting proteins in the Xenopus oocyte extract system, which is poised for rapid and efficient DNA replication. Baculovirus expressed recombinant DUE-B protein was added to a Xenopus oocyte high speed cytosol extract in the presence of protease inhibitors, and the mixture chromatographed on Sephacryl™ S-200. As shown in FIG. 16A, the exogenous rDUE-B eluted as a high molecular weight (>250 kDa) complex which could be detected with anti-DUE-B antibody but not preimmune serum (FIG. 16B). The same result was obtained whether the extract had been treated with RNase (FIGS. 16A and 16B) or not suggesting that the exogenous DUE-B was rapidly modified in the Xenopus extract or complexed with Xenopus proteins. In FIGS. 16A and 16B, DUE-B was mixed with Xenopus oocyte extract and the mixture chromatographed as in FIG. 8. Duplicate aliquots were separated by SDS-PAGE gels and Western blotted with preimmune antiserum or DUE-B antiserum. The profiles show that the exogenous DUE-B elutes with a molecular size of ca. 250 kDa while the putative endogenous crossreactive DUE-B (ca. 26 kDa) elutes as a ca. 54 kDa dimmer.

Figure 17:
FIG. 17 is a photograph showing the results of chromatography of recombinant (baculovirus expressed) DUE-B added to HeLa cell nuclear extract.

Note in FIG. 17 that a major portion of the recombinant DUE-B and a small, but reproducible amount of the endogenous DUE-B (HDUE-B) elute with a high molecular weight near the void volume of the column.

The anti-DUE-B antibody also detected a second band in the Xenopus cytosol preparation that eluted at an approximate molecular weight of 50 kDa. Based on its immunoreactivity with anti-DUE-B antibody but not preimmune serum, its molecular weight on SDS-PAGE (24 kDa) and its chromatographic elution as a ~50 kDa dimer, we speculate that this may represent the endogenous Xenopus DUE-B protein.

Figure 18A:
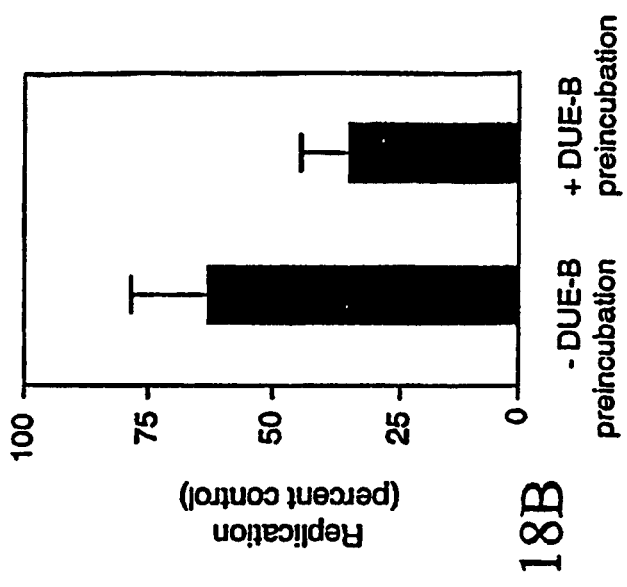
FIGS. 18A to 18D illustrate replication in *Xenopus oocyte* extracts.
Figure 18B:
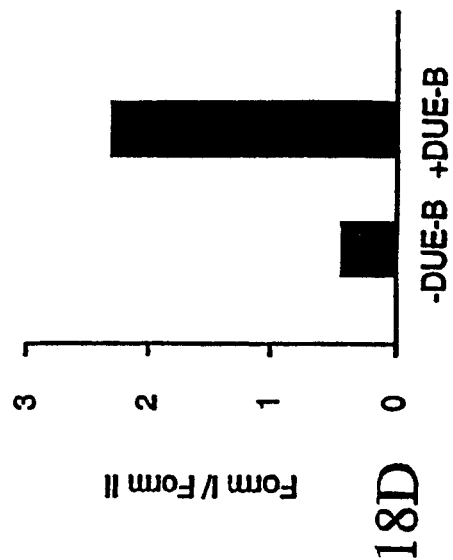
Figure 18C:
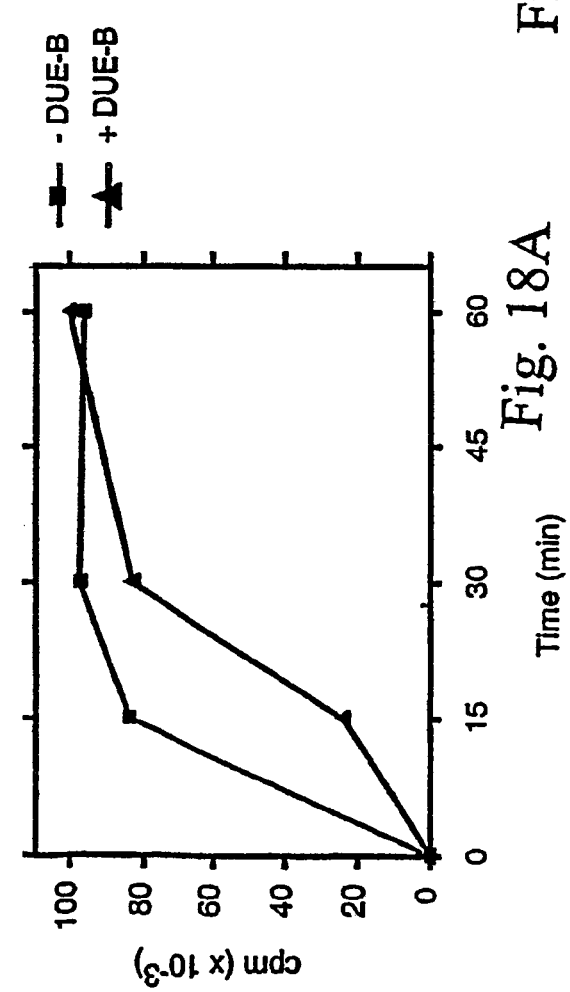
Figure 18D:
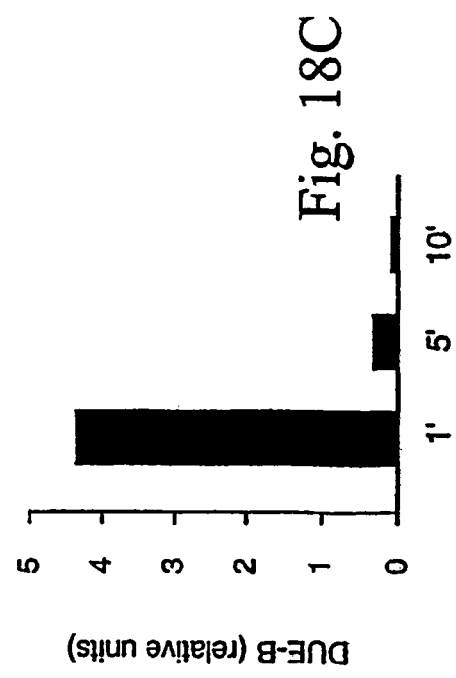

To test the effect of DUE-B on DNA replication, high molecular weight (phage lambda) DNA was preincubated in the Xenopus oocyte high speed extract. DUE-B was subsequently added with alpha-$^{32}$P-dCTP and an aliquot of the oocyte membrane fraction to yield a replication competent extract. A time course showed that DUE-B transiently inhibited DNA replication (FIG. 18A). In FIG. 18A, plasmid pNeo.Myc-2.4 DNA was incubated in oocyte extract for one hour prior to the addition of alpha-$^{32}$P-dCTP (=time zero) with or without the addition of DUE-B. When DUE-B was preincubated with the extract and DNA before the addition of alpha-$^{32}$P-dCTP and replication was assayed at 20 minutes, preincubation with DUE-B was seen to inhibit replication further (FIG. 18B). In FIG. 18B, phage lambda DNA was preincubated with Xenopus oocyte extract for one hour with or without DUE-B, prior to the addition of alpha-$^{32}$P-dCTP. Replication was measured 20 minutes after the addition of alpha-$^{32}$P-dCTP. A possible explanation for the transient inhibition of DNA replication by DUE-B is that the protein succumbs to degradation during incubation in the Xenopus extract. To test this directly, DUE-B protein levels were determined by Western blotting following addition of baculovirus expressed protein to the Xenopus extract. However, as seen in FIG. 18C, the exogenous DUE-B is stable in the extract, again suggesting that the exogenous DUE-B is rapidly modified when added to the Xenopus extract. In FIG. 18C, baculovirus expressed DUE-B (1 µg) was added to Xenopus extract and aliquots were removed at the indicated times for SDS-PAGE and Western blot analysis. The releative amount of DUE-B remaining at each time point has been corrected for the amount of Xenopus cross-reacting band co-migrating with the baculovirus DUE-B. To determine whether DUE-B has an effect on replication through an alteration in template structure, plasmid DNA was added to the Xenopus extract in the presence or absence of exogenous DUE-B. The addition of DUE-B increased the amount of supercoiled (form I) plasmid relative to nicked form II plasmid. Thus, one effect of DUE-B may be to increase DNA superhelicity in the extract, possibly by nucleosome loading (FIG. 18D). In FIG. 18D, plasmid DNA was added to the Xenopus extract in the absence or presence of DUE-B and analyzed by agarose gel electrophoresis. Addition of DUE-B increased the relative amount of supercoiled plasmid DNA.

Figure 19A:
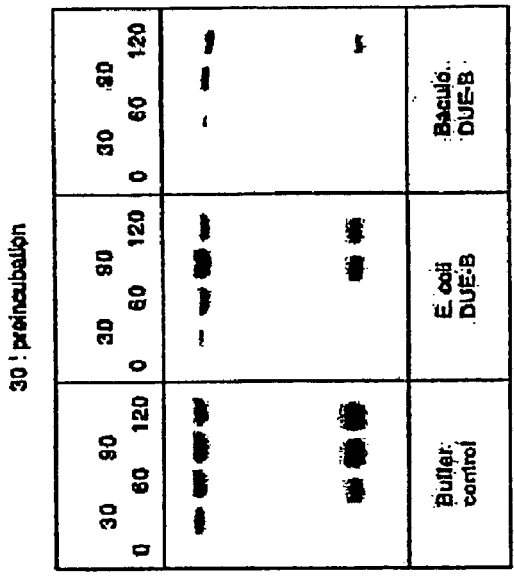
FIGS. 19A and 19B are photographs showing that baculovirus expressed DUE-B inhibits sperm chromatin replication.
Figure 19B:
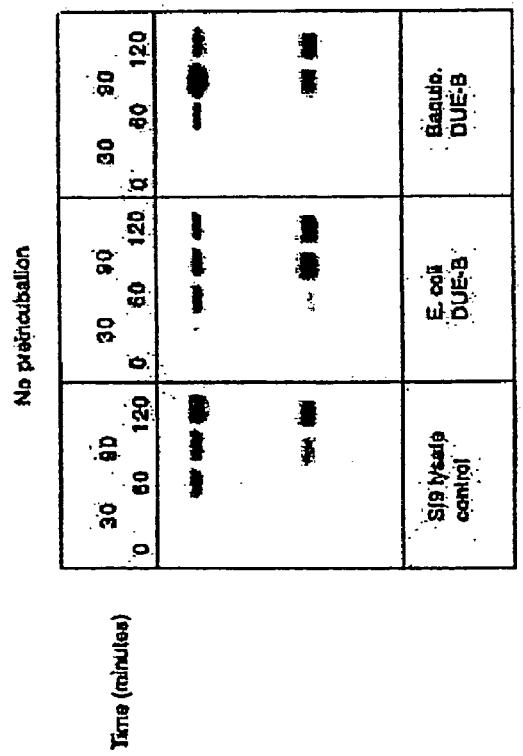
Figure 19C:
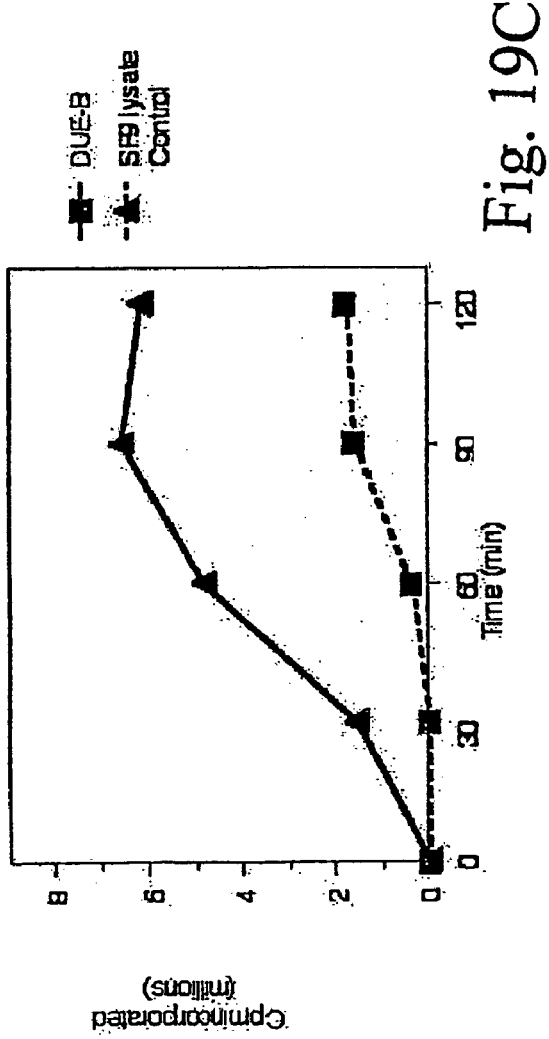
FIG. 19C is a graph showing the effect of 30' preincubation of extracts with control Sf9 lysate or recombinant DUE-B.

In FIGS. 19A to 19C, sperm chromatin and alpha-$^{32}$P-dCTP were added to Xenopus oocyte extracts in the presence or absence of DUE-B. The DNA was purified, electrophoresed on agarose gels, and the incorporated radiolabel quantitated. DUE-B expressed in baculovirus infected Sf9 cells was more effective at inhibiting replication of the natural oocyte substrate, sperm chromatin, when preincubated for 30' with the extract than when added simultaneously with the sperm chromatin.

In FIG. 20A, an ELISA assay shows that *Xenopus oocyte* extract reduces, but does not eliminate, saturable DUE-B binding to sperm chromatin. In FIG. 20B, oocyte extracts were centrifuged after the addition of sperm chromatin in the presence or absence of DUE-B. Pellets were immunoblotted with anti-MCM7 antibody. As can be seen from FIG. 20C, DUE-B does not inhibit MCM7 loading (prereplication complex [pre-RC] formation) on chromatin. In FIG. 20D, it can be seen that DUE-B does not inhibit replication of single stranded DNA in *oocyte* extract. These data suggest that DUE-B selectively inhibits replication of double stranded DNA, at a step after pre-RC formation.

Figure 21:
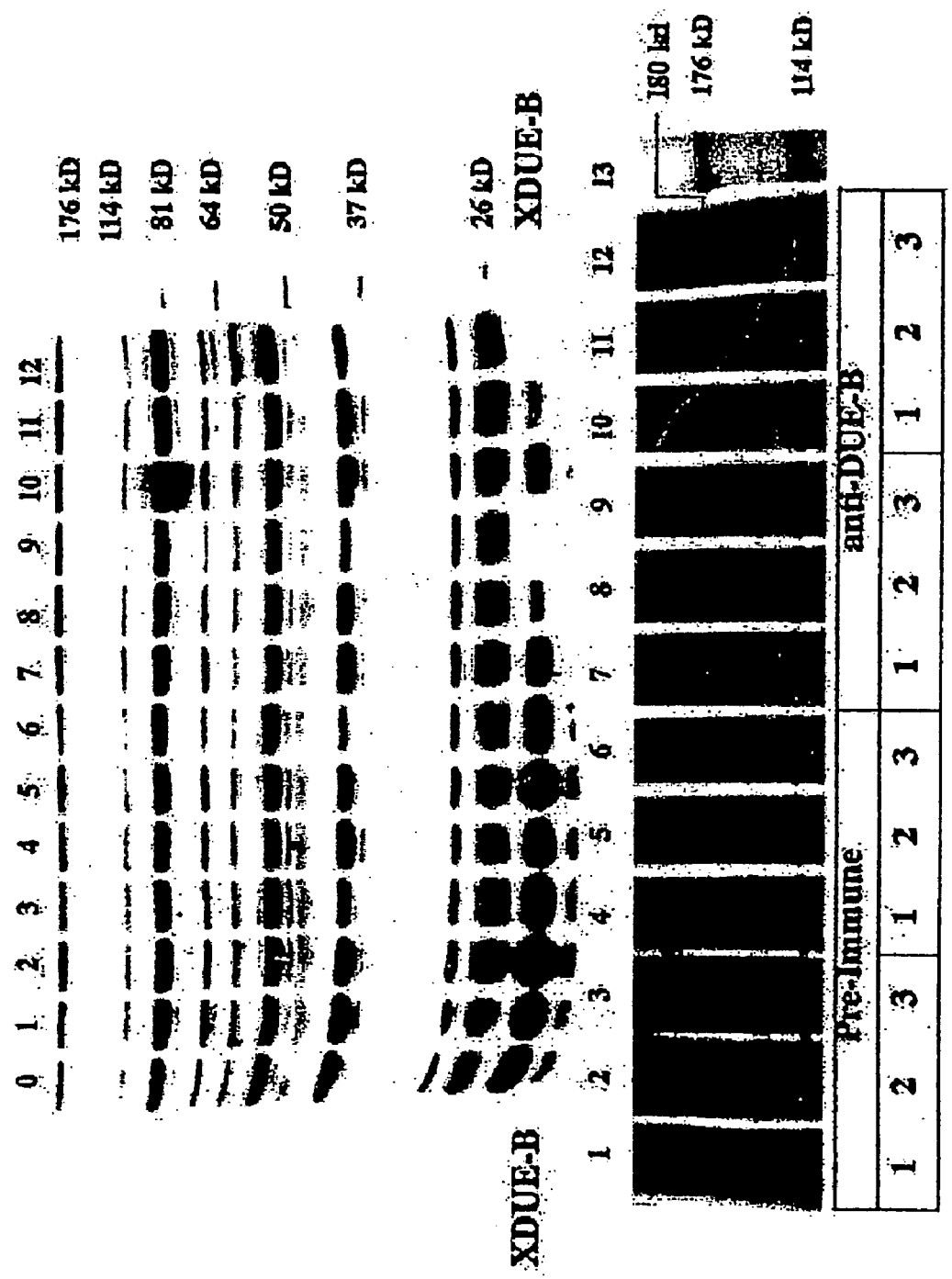
FIG. 21 demonstrates that DUE-B antibody co-immunoprecipitates a 180 kDa protein from *Xenopus* extracts.

FIG. 21 shows the results of immunodepletion of *Xenopus oocyte* replication extracts with anti-DUE-B antibody or preimmune serum. Note that the anti-human DUE-B antibody not only removes *Xenopus* DUE-B from the extract but selectively precipitates a 180 kDa protein not precipitated by the preimmune serum.

Steroid Binding of DUE-B

Figure 22B:
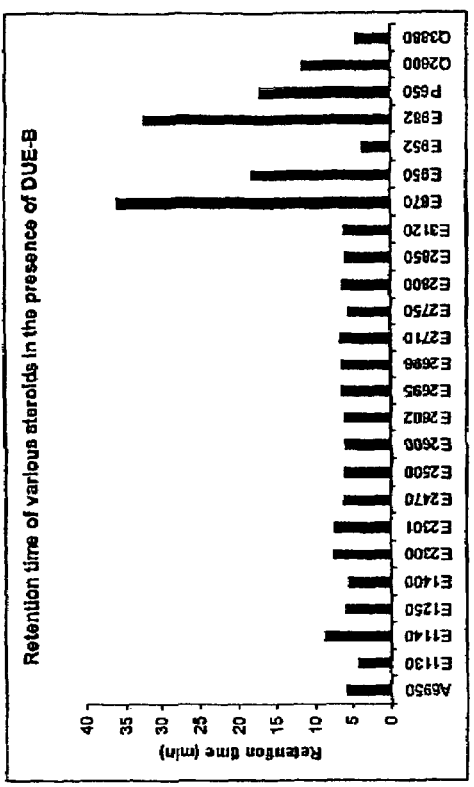
FIG. 22B shows the retention times measured for several different steroids.
Figure 22A:
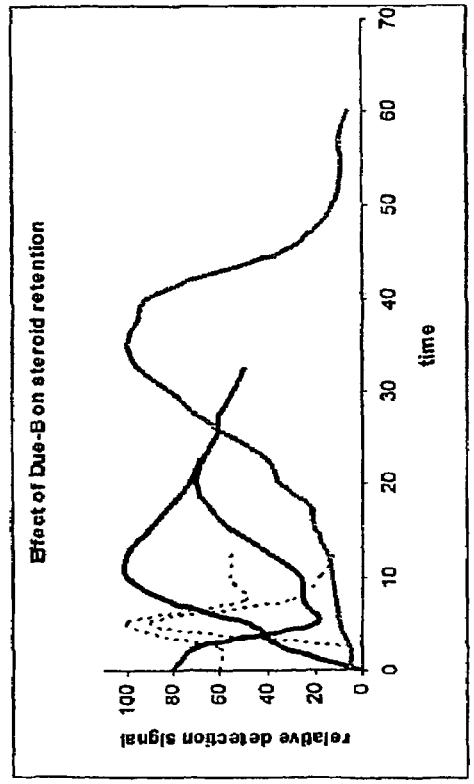
FIG. 22A shows typical results of chromatography experiments using steroids passed through the column in the absence of DUE-B (hashed lines) and in the presence of DUE-B (solid lines)

Steroid binding properties of DUE-B were assessed using purified 6his-V5 tagged DUE-B immobilized to a Nickel-Sepharose™ column (via the 6his tag) (FIGS. 22A and 22B). Steroids were passed through the column (50 ul of 100 nM) in the presence of 10 mM $NH_4OAc$ (pH 7.4) and 10% MeOH. Flow through was analyzed for steroid content by mass spectroscopy. Due to the fact that some steroids content by mass spectroscopy. Due to the fact that some steroids give a stronger signal by MS, signal strengths have been normalized to show the effects of DUE-B on steroid retention. Note that in the presence of DUE-B, some selected steroids have a much longer retention time in the column. This indicates a stronger association of these particular steroids with DUE-B. In FIG. 22B, note that marked increases in retention times are only seen with a subset of steroids, indicating that not only does DUE-B bind steroids, but it also displays selectively in the steroids it binds.

A Novel High Throughput Assay For Measuring DUE-B DNA Binding

Described herein is the first generation of a novel assay for determining the effects of molecules on the association of DUE-B with double stranded DNA (dsDNA). This assay uses fluorescence polarization to measure the interaction of DUE-B with dsDNA. This assay consists of 4 components:
 a) a dsDNA derived from the DUE sequence:

(SEQ ID NO:3)
(5'-GGAATATACA TTATATATTA AATATAGATC-3')

Both the sense and antisence strands are labeled with FITC at the 3' end using a 6 carbon spacer.
 b) Purified DUE-B. Human DUE-B tagged at the amino terminus with the 6his and V5 tags is synthesized in baculovirus and purified using $Ni^{2+}$-Sepharose™ chromatography.
 c) Reaction buffer (1x):100 mN Tris HCl (pH 7.5), 800 mM NaCl, 10 mM EDTA, 100 mM β-mercaptoethanol, 1% (w/v) Tween-20™.
 d) Fluorescence polarization plate reader (Tecan Polarion™ or other equivalent device)

Methodology

A mastermix is prepared consisting of 1x reaction buffer, 2 nM labeled oligo and 0.125 or 0.250 ug DUE-B per 100 ul of mastermix. Compounds (in this case steroids) are added to the bottom of a 96 well plate. 100 ul of mastermix is added to each well and allowed to equilibrate for 30 sec. Fluorescence polarization is then measured.

Figure 23A:
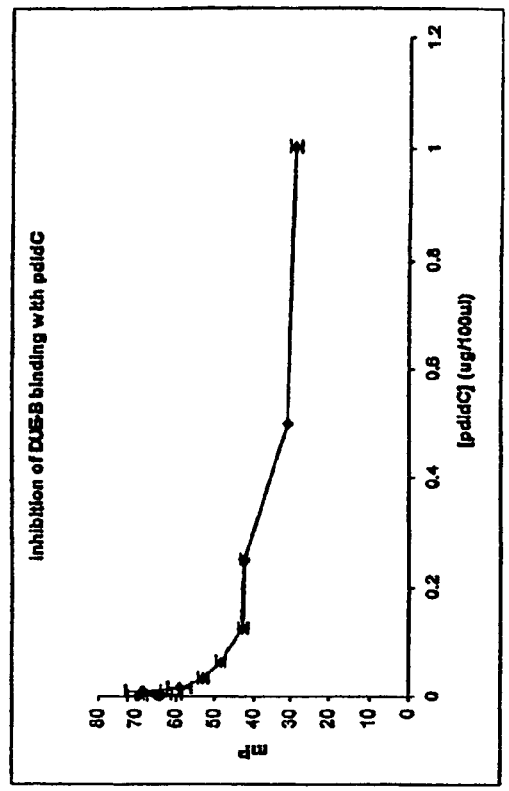
FIGS. 23A to 23C illustrate the development of the DUE-B assay designed in the present invention.
Figure 23B:
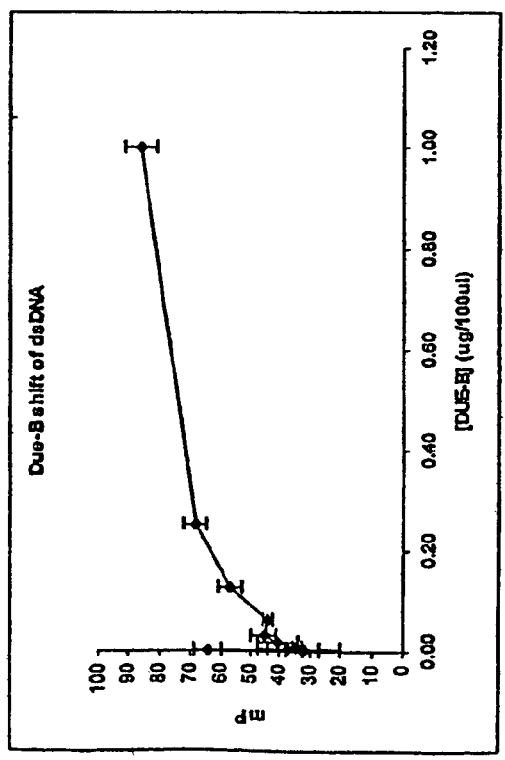
Figure 23C:
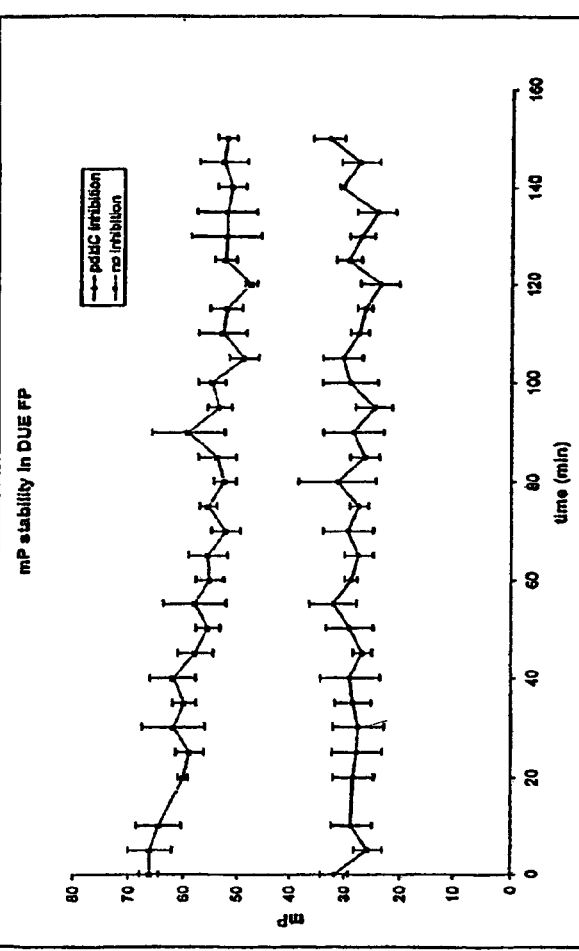

In FIG. 23A, the effect of increasing concentrations of DUE-B on the polarization of dsDNA was assessed. As expected, polarization of the dsDNA becomes saturated as the DUE-B protein concentration increases. Note that at 0.125 and 0.250 µg of DUE-B a reasonable shift in polarization of dsDNA is seen. Using these set conditions (0.250 µg DUE-B), the effect of adding a non-specific DNA inhibitor (pdIdC) to the reaction (FIG. 23B) was tested. The loss of dsDNA polarization in the presence of pdIdC indicates a reversible DNA association with DUE-B. FIG. 23C shows the temporal stability of these signals. It is observed that the polarization was stable for at least 2 hours, making this assay very feasible for high throughput screening.

Figure 24A:
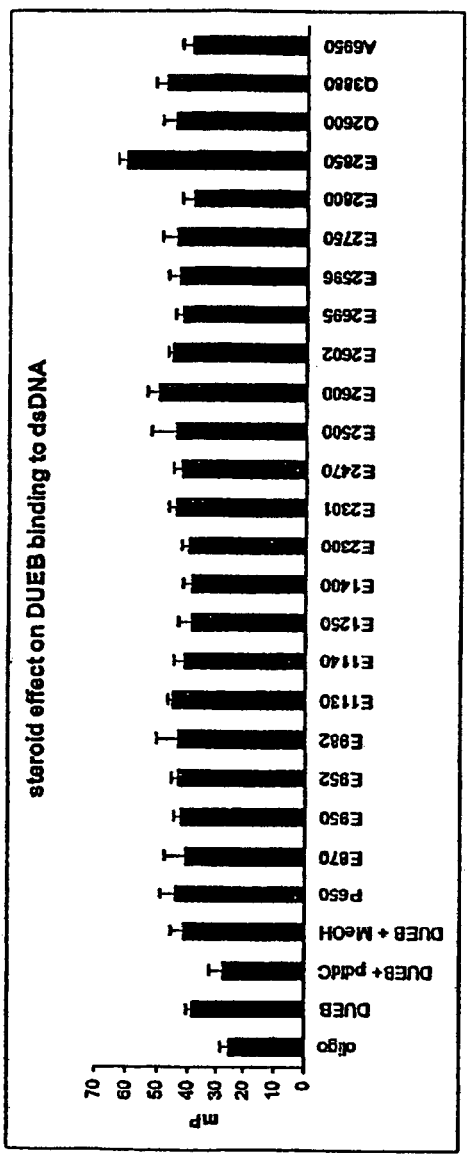
FIGS. 24A and 24B show a test screen using selected steroids to measure their effects on the binding of DUE-B to dsDNA.
Figure 24B:
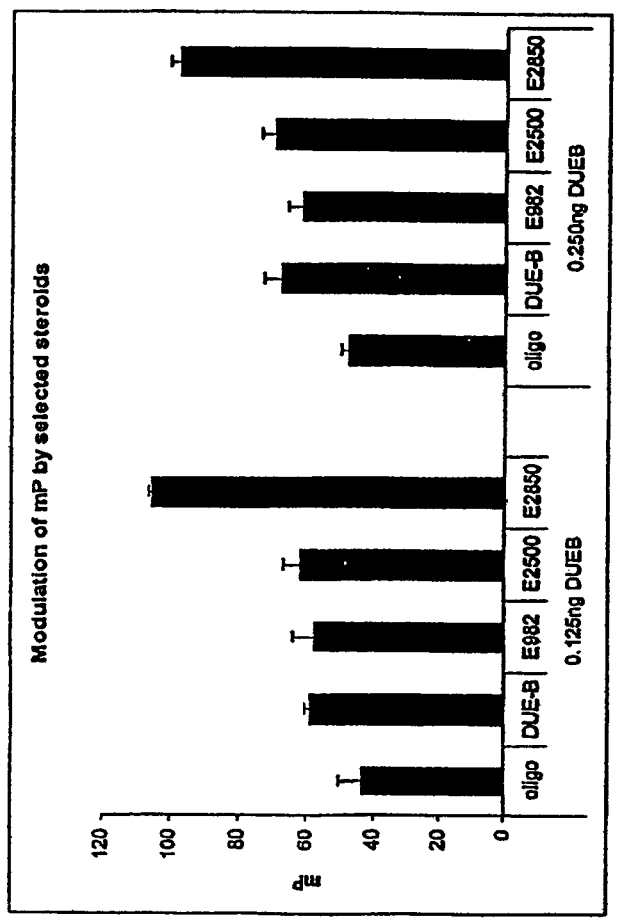

FIG. 24A shows the extent of polarization of dsDNA by DUE-B in the presence of different steroids at 10 uM. Note that E2850 gave a 100% increase in polarization, indicating a strong stimulatory effect on the dsDNA binding of DUE-B. FIG. 24B shows the validation of the results in FIG. 24A by retesting the compounds in two different concentrations of DUE-B. Here the stimulatory effect of E2850 was duplicated.

Discussion

In accordance with the present invention, a novel protein, DUE-B, has been isolated based on its selective affinity for the DUE/ARS sequence of the human c-myc replication origin in a yeast one-hybrid assay. Inasmuch as the c-myc DUE/ARS contains three matches to the yeast ARS consensus sequence, DUE-B is capable of binding to the DUE/ARS through direct association with DNA, through interaction with yeast origin binding proteins, or through a combination of forces. Interaction with origin DNA through secondary interactions with yeast proteins is suggested by the reduction in reporter expression when the ARS consensus elements of the DUE/ARS binding site were mutated. Sequencing and translation of the DUE-B cDNA predicts a protein of 209 amino acids, with a molecular weight of ca. 26 kDa. Northern blot analysis revealed a 1.35 kb mRNA, sufficient to encode a protein of 26 kDa and Western analysis using antibody raised against recombinant DUE-B cloned in bacteria detected the predicted ~26 kDa protein in HeLa cells. Screening of the NCBI Genbank database showed that highly homologous proteins are predicted to occur in bacteria, yeast, and mice. DUE-B mRNA and protein appear to be present at roughly constant levels throughout the cell cycle and agents that inhibit replication and elicit DNA damage response pathways (e.g. aphidicolin, hydroxyurea) did not affect the levels of DUE-B protein.

In the one-hybrid assay a nuclear localization signal becomes part of the HeLa library proteins expressed in the reporter yeast. Immunocytochemical analysis showed that DUE-B expressed in HeLa cells localized to the nucleus in the absence of an exogenous nuclear localization sequence. This observation was consistent with data showing that a fraction of endogenous DUE-B could be recovered from nuclei isolated after HeLa cell lysis and released from the nuclei by salt or DNase extraction.

DUE-B cloned and expressed in bacteria chromatographed as a ~26 kDa monomer on gel exclusion chromatography, while DUE-B cloned in a baculovirus vector and expressed in insect cells eluted as a ~50 kDa dimer, suggesting that expression in the eukaryotic insect cells may result in a different posttranslationally modified form of the protein, and that the posttranslational modification may influence DUE-B function. Chromatography of HeLa extracts also revealed the ~50 kDa dimeric form of the endogenously synthesized DUE-B, along with a minor amount of DUE-B protein eluting at higher molecular weight (>250 kDa). When baculovirus expressed DUE-B was mixed with *Xenopus oocyte* extracts or HeLa extracts virtually all of the added DUE-B was found to elute as the high molecular weight protein complex. In contrast, the putative *Xenopus* or HeLa DUE-B proteins eluted at the ~50 kDa dimer position. These data suggest that the structure of the exogenous HeLa DUE-B protein may be modified in the *Xenopus* or HeLa extracts, which results in its association to a high molecular weight protein complex.

A prevalent modification of proteins involved in the assembly of replicative complexes is transient phosphorylation. Despite the presence of seven casein kinase consensus target sites, radiolabeling of HeLa cells with $^{32}$P-orthophosphate did not reveal in vivo phosphorylation of immunoprecipitated DUE-B. However, since immunoprecipitated HeLa DUE-B or baculovirus expressed DUE-B could be phosphorylated in vitro by copurifying kinases, it remains possible that DUE-B undergoes transient phosphorylation in vivo.

Proteins that bind and hydrolyze ATP are common in the initiation of DNA replication. Consistent with the prediction of ATP and GTP binding domains in DUE-B, chromatography of the baculovirus expressed protein showed that the DUE-B dimer co-eluted with ATPase activity. Under the present assay conditions DUE-B hydrolyzed>0.5 fmol ATP per minute per fmol protein. For comparison, the calculated Vmax of purified yeast ORC is 0.27 fmol ATP hydrolyzed per min per fmol protein.

The binding of DUE-B to DNA in EMSA could be reversed by nonspecific competitor, suggesting that DUE-B possess a nonspecific affinity for DNA. Similar binding has been observed for the yeast ORC. However, in the presence of cytoplasmic or nuclear extracts, DUE-B appeared to form heteromeric complexes that were resistant to nonspecific competition. The ability to form high molecular weight complexes was implied by the presence of a small amount of early eluting DUE-B in HeLa extracts, and the early elution of DUE-B added exogenously to *Xenopus oocyte* extracts. The data obtained in accordance with the present invention also suggest that the anti-DUE-B antibody may have uncovered a crossreacting *Xenopus* homolog of DUE-B, and that these proteins may undergo distinct modifications that affect their structure and function in the *Xenopus* extract. The association of DUE-B with heterologous proteins in solution or bound to c-myc origin DNA suggests that methods for detecting protein-protein interactions (yeast two-hybrid system, affinity chromatographic co-purification, co-immunoprecipitation) may reveal natural binding partners that interact with DUE-B to affect the initiation of DNA replication.

Materials and Methods

Yeast One-hybrid Assay

The wild type DUE/ARS region of the c-myc origin (nt 735-832; Genbank accession number X00364) was cloned into the vector pHisi-1 and transformed into *S. cerevisiae* strain YM4271 (MATa, ura3-52, his3-200, ade2-101, lys2-801, leu2-3, 112, trp1-901, tyr1-501, gal4-D512, gal80-D538, ade5::hisG) according to the manufacturer's directions. The wild type and mutant DUE/ARS bait sequences are as follows:

```
Wild type:
ATGAGAAGAA TGTTTTTTGT TTTTCATGCC GTGGAATAAC ACAAAATAAA  (SEQ ID NO:4)
AAATCCCGAG GGAATATACA TTATATATTA AATATAGATC ATTTCAGG.

ARS mutant:
ATGAGAAGAA TGTTTTTTGC GCTTCATGCC GTGGAATAAC ACAGCGTAAA  (SEQ ID NO:5)
AAATCCCGAG GGAATATACA TTATATATTT GTTATAGATC ATTTCAGG.

DUE mutant/ARS mutant:
ATGAGAAGAA TGTTTTTTGC GCTTCATGCC GTGGAATAAC ACAGCGTAAA  (SEQ ID NO:6)
AAATCCCGAG GGAATGCACA TTGCATATTG CGCGTACGAT CATTTCAGG.
```

Transformants were selected for growth on his-medium (Clontech). The reporter strain was transformed with a HeLa cDNA library cloned in pGAD-GH (Clontech Matchmaker) and colonies selected for growth at 30° C. on his-, leu-medium containing 15 mM 3-aminotriazole (3-AT). Plasmid was isolated from crude yeast lysates and cloned in *E. coli* according to standard procedures. DNA was sequenced on an Applied Biosystem 377 DNA Sequencer.

DUE-B Protein and mRNA Analysis

The cDNA insert of plasmid pGK16B encoding the DUE-B protein with a C-terminal his6 tag was cloned by PCR, inserted into the bacterial expression vector pTRC-His and expression in *E. coli* was induced by IPTG. The protein was isolated on Ni-NTA columns (Qiagen) under non-denaturing conditions following the manufacturer's instructions. Polyclonal antibody to DUE-B was produced commercially (Cocalico Corp) by injection of bacterial expressed DUE-B into rabbits. HeLa cells were synchronized in S phase (1 µg/ml aphidicolin or 2 mM hydroxyurea, overnight), M phase (100 ng/ml or 400 ng/ml nocodazole, overnight). HeLa cells were lysed using Popper buffers (Pierce) to yield nuclear and cytoplasmic fractions. Western blotting was performed on proteins resolved on 12% SDS-PAGE gels transferred to Immobilon™ membranes by standard procedures. For expression in insect cells using the MaxBac™ kit (Invitrogen) DUE-B cDNA was cloned into the pBlueBac4.5 vector and cotransformed with Bac-N-Blue AcMNPV DNA into SF9 cells according to the manufacturer's directions.

Purified DUE-B (200-1000 ng) expressed in bacteria or insect cells, or cell extracts from HeLa cells (~500 ng) or *Xenopus oocytes* (~500 ng), were chromatographed on a one-meter Sephacryl™ S-200 column. Protein elution was monitored by Western blot or by ELISA using antibodies to DUE-B or the his6 tag. ATPase activity was monitored by thin layer chromatography on PEI cellulose (Patrick, S. M., et al., *Biochem. Biophys. Acta* 1354:279-290, 1997). RNA was isolated using an RNAeasy kit (Qiagen) and DUE-B mRNA expression was monitored by Northern blotting of total RNA electrophoresed on denaturing formaldehyde/agarose gels using a DUE-B cDNA probe labeled with alpha-$^{32}$P-dCTP by random primer extension.

Immunocytochemistry

DUE-B cDNA including myc and his6 epitope tags was subcloned into the eukaryotic expression vector pcDNA3.1 and transfected into HeLa cells. Forty-eight hours post-transfection the cells were fixed, permeabilized, and incubated with FITC conjugated antibody specific for the myc epitope. Cells were counterstained with Hoechst™ 33258 dye.

EMSA

A 123 bp fragment containing the c-myc DUE/ARS was labeled by PCR in the presence of alpha-$^{32}$P-dCTP. The sequence of the probe is: GAAGGAATTC ATGAGAAGAA TGTTTTTTGT TTTTCATGCC GTGGAATAAC ACAAAATAAA AAATCCCGAG GGAATATACA TTATATATTA AATATAGATC ATTTCAGGGA GCTC-GAGAAA CAA (SEQ ID NO:7).

Recombinant DUE-B was obtained from SF9 insect cells and purified by Ni-NTA affinity chromatography. Binding reactions were performed at 30° for 30 minutes and separated by 4% native PAGE at room temperature in 0.5×TBE buffer prior to autoradiography.

Replication in *Xenopus oocyte* Extracts

*Oocyte* extracts were prepared according to published procedures and the replication of plasmid pNeo.Myc-2.4 or phage lambda DNA monitored in the presence of alpha-$^{32}$P-dCTP as described in Walter, J., and J. Newport (Walter, J., and J. Newport, *Mol. Cell* 5:617-627, 2000) and in Walter, J., et al., (Water, J., et al., *Mol. Cell* 1:519-529, 1998)

The specific illustrations and embodiments described herein are exemplary only in nature and are not intended to be limiting of the invention defined by the claims. Further embodiments and examples will be apparent to one of ordinary skill in the art in view of this specification and are within the scope of the claimed invention.

What is claimed is:

1. A method for screening compounds capable of modulating cell proliferation, comprising:
   a) contacting in a medium a compound to be screened with a peptide comprising an amino acid sequence as set forth in SEQ ID NO:2, the peptide bindable to a c-myc replication origin polynucleotide sequence;
   wherein the medium comprises a polynucleotide comprising a sequence of a c-myc replication origin;
   b) determining binding of said compound to said peptide; and
   c) determining change in binding of said peptide to said polynucleotide;
   wherein detection of binding of said compound to said peptide and change in binding of said peptide to said polynucleotide is indicative that said compound is capable of modulating cell proliferation.

2. A method according to claim 1 for identifying a compound capable of inhibiting cell proliferation, comprising detecting binding of the compound to be screened to said peptide and inhibition of binding of said peptide to said polynucleotide.

3. A method according to claim 1, wherein the peptide is a polypeptide.

4. A method according to claim 3, wherein the polypeptide is DNA Unwinding Element Binding Protein.

5. A method according to claim 1, wherein the compound to be screened is a steroid.

6. A method according to claim 1 for screening anticancer agents.

7. A method according to claim 1, wherein the polynucleotide comprises a sequence of a c-myc replication origin DNA Unwinding Element, and the peptide is bindable thereto.

8. A method according to claim 7, wherein the polynucleotide comprises a sequence as set forth in SEQ ID NO: 4.

9. A method according to claim 7, wherein the polynucleotide comprises a sequence as set forth in SEQ ID NO: 3.

10. A method for screening compounds capable of modulating cell proliferation, comprising:
   a) contacting in a medium a compound to be screened with a peptide comprising an amino acid sequence as set forth in SEQ ID NO:2, the peptide bindable to a c-myc replication origin DNA Unwinding Element polynucleotide sequence;
   wherein the medium comprises a polynucleotide comprising a sequence of a c-myc replication origin DNA Unwinding Element;
   b) determining binding of said compound to said peptide; and
   c) determining change in binding of said peptide to said polynucleotide;

wherein detection of binding of said compound to said peptide and change in binding of said peptide to said polynucleotide is indicative that said compound is capable of modulating cell proliferation.

11. A method according to claim 10 for identifying a compound capable of inhibiting cell proliferation, comprising detecting binding of the compound to be screened to said peptide and inhibition of binding of said peptide to said polynucleotide.

12. A method for screening compounds capable of inhibiting cell proliferation, comprising:
   a) contacting in a medium a compound to be screened with a peptide comprising an amino acid sequence as set forth in SEQ ID NO:2, the peptide bindable to a polynucleotide comprising a sequence as set forth in SEQ ID NO: 4;
      wherein the medium comprises a polynucleotide comprising a sequence as set forth in SEQ ID NO: 4;
   b) determining binding of said compound to said peptide; and
   c) determining inhibition of binding of said peptide to said polynucleotide;
   wherein detection of binding of said compound to said peptide and inhibition of binding of said peptide to said polynucleotide is indicative that said compound is capable of inhibiting cell proliferation.

* * * * *